(12) United States Patent
Bonny

(10) Patent No.: US 7,943,574 B2
(45) Date of Patent: May 17, 2011

(54) CELL-PERMEABLE PEPTIDE INHIBITORS OF THE JNK SIGNAL TRANSDUCTION PATHWAY

(75) Inventor: Christophe Bonny, Morges (CH)

(73) Assignee: Xigen SA, Lausanne (CH)

( * ) Notice: Subject to any disclaimer, the term of this patent is extended or adjusted under 35 U.S.C. 154(b) by 70 days.

(21) Appl. No.: 12/552,337

(22) Filed: Sep. 2, 2009

(65) Prior Publication Data
US 2010/0056459 A1 Mar. 4, 2010

Related U.S. Application Data

(62) Division of application No. 10/500,804, filed as application No. PCT/IB03/00332 on Jan. 9, 2003, now Pat. No. 7,635,681.

(60) Provisional application No. 60/347,062, filed on Jan. 9, 2002.

(51) Int. Cl.
*A61K 38/17* (2006.01)
*A61K 38/21* (2006.01)
*C07K 14/16* (2006.01)
*C07K 14/47* (2006.01)

(52) U.S. Cl. ....... 514/8.3; 514/21.3; 514/21.4; 530/324; 530/325; 530/326

(58) Field of Classification Search .................. None
See application file for complete search history.

(56) References Cited

U.S. PATENT DOCUMENTS

| 4,631,211 | A | 12/1986 | Houghten |
| 6,348,185 | B1 | 2/2002 | Piwnica-Worms |
| 6,653,443 | B2 | 11/2003 | Zhang et al. |

FOREIGN PATENT DOCUMENTS

| WO | WO 94/04686 | 3/1994 |
| WO | WO 98/47913 | 10/1998 |
| WO | WO 98/49188 | 11/1998 |
| WO | WO 99/50282 | 10/1999 |
| WO | WO 99/58561 | 11/1999 |
| WO | WO 01/27268 | 4/2001 |
| WO | WO 02/81504 | 10/2002 |

OTHER PUBLICATIONS

Negri et al. Diabetes, A Journal of the American Diabetes Association, vol. 50, Supplement 2, Abstract Book for the 61st Scientific Sessions, Pennsylvania Convention Center, Jun. 2001, p. A294.*
Abaza et al. "Effects of amino acid substitutions outside an antigenic site on protein binding to monoclonal antibodies of predetermined specificity obtained by peptide immunization: demonstration with region 94-100 (antigenic site 3) of myoglobin" J. Protein Chem. 11(5), pp. 433-444 (1992).
Agrawal et al. "Promiscuous binding nature of SH3 domains to their target proteins", Protein Pept. Lett., 9(3):185-193 (2002).
Bonny et al. "Cell-permeable peptide inhibitors of JNK: novel blockers of beta-cell death", Diabetes, 50(1):77-82 (2001).
Borsello et al. "A peptide inhibitor of c-Jun N-terminal kinase protects against excitotoxicity and cerebral ischemia", Nat Med. 9(9), pp. 1180-1186 (2003).
Creighton, T. Encyclopedia of Molecular Biology, John Wiley and Sons, Inc. New York, pp. 2027-2033 (1999).
Fawell et al. "Tat-mediated delivery of heterologous proteins into cells" Proc. Natl. Acad. Sci. USA. 91(2), pp. 664-668 (1994).
GenBank Database Accession No. PH0878, May 1997.
Huq et al. "Specific recognition of HIV-1 TAR RNA by a D-Tat peptide", Nat Struct Biol. 4(11), pp. 881-882 (1997).
Houghten, "General method for the rapid solid-phase synthesis of large numbers of peptides: specificity of antigen-antibody interaction at the level of individual amino acids", Proc. Natl. Acad. Sci. USA, 82(15):5131-5135 (1985).
International Search Report for PCT/IB03/00332, mailing date: Jul. 19, 2004.
Kishan et al. "SH3-like fold proteins are structurally conserved and functionally divergent", Curr. Protein Pept. Sci., 6(2):143-150 (2005).
Li, S. "Specificity and versatility of SH3 and other proline-recognition domains: structural basis and implications for cellular signal transduction", Biochem. J., 390(Pt 3):641-653 (2005).
Mayer et al.: "SH3 domains: complexity in moderation", J. Cell Science, vol. 114(7), pp. 1253-1263, 1997.
Moulin et al. "Islet-brain (IB)/JNK—interacting proteins (JIPs): future targets for the treatment of neurodegenerative diseases?", Curr. Neurovasc. Res., 1(2):111-127 (2004).
Rickles et al. "Phage display selection of ligand residues important for Src homology 3 domain binding specificity", 92(24): 10909-10913 (1995).
Stevens et al., "Peptide length preferences for rat and mouse MHC class I molecules using random peptide libraries", Eur. J. Immunol., 28(4):1272-1279 (1998).
Stevens et al., "Efficient generation of major histocompatibility complex class I-peptide complexes using synthetic peptide libraries", J. Biol. Chem., 273(5):2874-2884 (1998).
Vives et al. "A truncated HIV-1 Tat protein basic domain rapidly translocates through the plasma membrane and accumulates in the cell nucleus", J. Biol. Chem., 272(25):16010-16017 (1997).
Waldmeir et al (2006). Biochemical Pharmacology. 72, 1197-1206.
Bonny et al., "IB1, a JIP-1-related nuclear protein present in insulin-secreting cells", J. Biol. Chem., 273(4): 1843-1846 (1998).

* cited by examiner

*Primary Examiner* — Jeffrey Stucker
*Assistant Examiner* — Stephen Gucker
(74) *Attorney, Agent, or Firm* — Morgan, Lewis & Bockius LLP

(57) ABSTRACT

The invention provides cell-permeable peptides that selectively block the branch of the JNK signaling pathway controlled by the islet-brain (IB) proteins. The provided cell-permeable peptides block the binding of intermediate kinases in the c-Jun amino terminal kinase (JNK) signaling pathway, thereby decreasing the downstream effects of c-Jun amino terminal kinase (JNK).

4 Claims, 9 Drawing Sheets

| | | | | | | | | | | | | | | | | |
|---|---|---|---|---|---|---|---|---|---|---|---|---|---|---|---|---|
| S | S | V | S | P | V | V | G | M | K | P | S | P | R | P | 26 | (SEQ ID NO:7) |
| S | S | V | S | P | V | V | G | N | P | S | P | R | H | | 2 | (SEQ ID NO:8) |
| T | Q | P | M | L | A | H | M | C | A | P | P | S | P | R | Q | 1 | (SEQ ID NO:9) |
| L | L | D | S | L | F | Q | L | P | F | P | S | P | R | P | 1 | (SEQ ID NO:10) |
| | H | P | G | L | Q | P | S | Q | S | P | P | R | S | 1 | (SEQ ID NO:11) |
| | | | S | | | L | S | P | P | T | S | F | R | | 1 | (SEQ ID NO:12) |
| F | N | P | W | S | S | G | S | N | P | P | S | L | L | R | | 1 | (SEQ ID NO:13) |
| N | A | S | V | M | G | A | K | P | N | L | N | L | | 1 | (SEQ ID NO:14) |
| E | H | M | A | L | T | D | H | L | S | H | | 1 | (SEQ ID NO:15) |
| | | | | | | G/L | x | P | P | S | R | P | | 1 | (SEQ ID NO:16) |
| | | | | | | | Y | P | F | R | P | | 1 | (SEQ ID NO:17) |
| CONSENSUS | S | x | S/P | V | G/L | x | P | P | S | R | P | | 37 | (SEQ ID NO:2) | | |
| αSH3 | S | V | S | G | M | P | P | S | R | P | | 1 | (SEQ ID NO:1) | | | |
| CONSENSUS SH3 | | | | | P | X | X | P | X | P | | (SEQ ID NO:35) | | | | |

FIG. 1

CELL-PERMEABLE PEPTIDE INHIBITORS OF THE JNK SIGNAL TRANSDUCTION PATHWAY

The present application is a divisional of U.S. Ser. No. 10/500,804, filed Jan. 7, 2005, now U.S. Pat. No. 7,635,681, which is a national stage application, filed under 35 U.S.C. 371, of International Application No. PCT/IB03/00332, filed Jan. 9, 2003, which claims the benefit of U.S. Provisional Application No. 60/347,062, filed Jan. 9, 2002, all of which are hereby incorporated by reference.

FIELD OF THE INVENTION

This invention relates generally to protein kinase inhibitors and more specifically to inhibitors of the protein kinase c-Jun amino terminal kinase signal transduction pathway.

BACKGROUND OF THE INVENTION

The c-Jun amino terminal kinase (JNK) is a member of the stress-activated group of mitogen-activated protein (MAP) kinases. The JNK signal transduction pathway is activated in response to environmental stress and by several classes of cell surface receptors, such as for example, cytokine receptors, serpentine receptors, and receptor tyrosine kinases. JNK is activated by dual phosphorylation that is mediated by a protein kinase cascade that consists of a MAP kinase (MAPK), a MAP kinase kinase (MAPKK), and a MAP kinase kinase kinase (MAPKKK). Targets of the JNK signaling pathway include transcriptions factors, such as for example, the transcription factors ATF2 and c-Jun.

These kinases have been implicated in the control of cell growth and differentiation, and, more generally, in the response of cells to environmental stimuli. In mammalian cells, JNK has been implicated in such biological processes as oncogenic transformation and in mediating adaptive responses to environmental stress. JNK has also been associated with modulating immune responses, including maturation and differentiation of immune cells, as well effecting programmed cell death in cells identified for destruction by the immune system.

Studies have implicated the JNK signaling pathway in apoptosis and survival signaling, and in particular, JNK has been recognized as a component of the stress-induced apoptotic signaling mechanism. Studies have shown that JNK is required for the stress-induced release of mitochondrial cytochrome c, and therefore, JNK is required for stress-induced apoptosis that is mediated by the mitochondrial/caspase-9 pathway.

SUMMARY OF THE INVENTION

The present invention is based in part on the discovery of cell-permeable peptides that selectively block the branch of the JNK signaling pathway controlled by the islet-brain (IB) proteins (also referred to as insulin binding (IB) proteins). The peptides, referred to herein as SH3 binding peptides (SH3-BP), block the binding of intermediate kinases in the c-Jun amino terminal kinase (JNK) signaling pathway, thereby decreasing the downstream effects of c-Jun amino terminal kinase (JNK).

Accordingly, the invention includes novel SH3 binding peptides, as well as chimeric peptides which include an SH3 binding peptide linked to a trafficking peptide that can be to used to direct a peptide on which it is present to a desired cellular location. The trafficking sequence can be used to direct transport of the peptide across the plasma membrane. Alternatively, or in addition, the trafficking peptide can be used to direct the peptide to a desired intracellular location, such as the nucleus.

In its various aspects, the invention includes an SH3 binding peptide having the amino acid sequence of SEQ ID NO: 1-35. The SH3 binding peptide binds an islet-brain (IB) polypeptide, such as IB1 or IB2. Alternatively, the SH3 binding peptide inhibits the binding of an MKK7 kinase to an SH3 domain polypeptide. The SH3 binding peptide is less than 500 amino acids in length, e.g., less than or equal to 400, 300, 200, 100, 50 or 25 amino acids in length.

In another aspect, the invention includes a chimeric peptide having a first domain and a second domain that are linked by a covalent bond, such that the first domain includes an amino acid sequence derived from the human immunodeficiency virus (HIV) 1 TAT polypeptide and the second domain includes an SH3 binding peptide, e.g., SEQ ID NO: 1-35. A chimeric peptide includes for example SEQ ID NO: 3-4 and 20-21. In some aspects, the SH3 binding peptide binds an islet-brain (IB) polypeptide.

In another aspect, the invention includes a peptide having an SXSVGX (SEQ ID NO: 5) motif and a PPSPRP (SEQ ID NO: 6) motif, and binds an SH3 domain polypeptide, such as an islet-brain (IB) polypeptide. Preferably, the peptide is less than 50 amino acids in length. In some aspects, the peptide includes the trafficking sequence of SEQ ID NO: 36.

The SH3 binding peptides can be present as polymers of L-amino acids. Alternatively, the peptides can be present as polymers of D-amino acids. In another embodiment, the peptides can be present as retro-inverso isomers of a peptide.

Also included in the invention are pharmaceutical compositions that include the SH3 binding peptides, as well as antibodies that specifically recognize the SH3 binding peptides.

In another aspect, the invention includes an isolated nucleic acid that encodes an SH3 binding peptide containing the amino acid sequence of SEQ ID NO: 1-35. The invention also includes a vector containing the isolated nucleic acid that encodes an SH3 binding peptide containing the amino acid sequence of SEQ ID NO: 1-35, as well as a cell that contains such a vector.

In another aspect, the invention includes a method of inhibiting apoptosis in a cell, e.g., a pancreatic cell or a neuronal cell, by contacting the cell with an SH3 binding peptide of the invention, e.g., SEQ ID NO: 2. The cell is a neuronal cell or a pancreatic cell. In another embodiment, the cell is contacted either in vitro, in vivo, or ex vivo.

Also included in the invention is a method of alleviating a symptom of an apoptosis-associated disorder, e.g., a neurological disorder, a neurodegenerative disorder, or a pancreatic disorder, in a subject by administering a SH3 binding peptide of the invention. For example, the subject is administered a polypeptide containing the amino acid sequence of SEQ ID NO: 2.

In another aspect, the invention includes a method of promoting neuronal cell growth or regeneration by contacting a neuronal cell with a SH3 binding protein, e.g., SEQ ID NO: 2.

Among the advantages provided by the invention is that the SH3 binding peptides are small, and can be produced readily in bulk quantities and in high purity. The binding peptides are also resistant to intracellular degradation, and are weakly immunogenic. Accordingly, the peptides are well suited for in vitro and in vivo applications in which inhibition of JNK-signaling is desired.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In the case of conflict, the present specification, including definitions, will control. In addition, the materials, methods, and examples are illustrative only and not intended to be limiting.

Other features and advantages of the invention will be apparent from the following detailed description and claims.

BRIEF DESCRIPTION OF THE DRAWINGS

FIG. 1 is a diagram showing alignments of amino acid sequences that bind the SH3 domain of IB1/2.

DETAILED DESCRIPTION OF THE INVENTION

Figure 2:
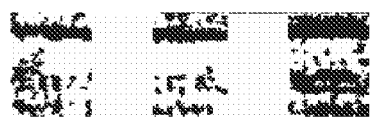
FIG. 2 is an illustration demonstrating the effects of IB, IB2, IB1-TAT$_{(1\ \mu M)}$, IB1-TAT-αSH3$_{(0.1\ \mu M)}$, IB1-TAT-αSH3$_{(1\ \mu M)}$, IB2-TAT-αSH3$_{(1\ \mu M)}$ on MKK7 binding to IB1/2.

The present invention is based in part on the discovery of cell permeable peptides that inhibit the branch of the activated c-Jun amino terminal kinase (JNK) signaling pathway that is controlled by the islet-brain (IB) proteins (also referred to as insulin binding (IB) proteins). These cell-permeable peptides are referred to herein as SH3 binding peptides (SH3-BP). Additionally, the discovery provides methods of inhibiting apoptosis and methods and pharmaceutical compositions for treating or alleviating a symptom of an apoptosis-associated disorders. The discovery further provides methods of promoting (i.e., increasing) neuronal cell growth and regeneration. By cell permeable it is meant that the peptides are capable of crossing a biological membrane, such as a cellular or nuclear membrane.

Mitogen-activated protein kinase (MAPK) pathways, such as the extracellular-regulated kinases (ERKs)-1/2, p38 kinases, and the c-Jun NH$_2$-terminal kinases (JNKs) signaling pathway, have a core unit formed by a three-member protein kinase cascade. Within the three-kinase module, the MAPK is phosphorylated and activated by MAPK kinases, known as MKKs. Typically, the MKKs are dual specificity kinases that catalyze the phosphorylation of MAPKs on both tyrosine and threonine residues. In turn, the MKKs are phosphorylated and activated by serine/threonine kinases that function as MKK kinases, known as MKKKs. See Garrington, et al., Curr. Op. in Cell Biol. 11:211-218 (1991).

In the JNK signaling pathway, this protein kinase cascade is formed by three sequential kinases, known as MLK, MKK7 and JNK. These three sequential kinases interact with, and are organized by, scaffold proteins known as the insulin-binding, or islet-brain, (IB) proteins. The IB proteins are transcription factors that exhibit sequence-specific DNA binding activity. IB1 is a transcriptional activator that is involved in the control of the glucose transporter gene GLUT2 and insulin genes, through interaction with homologous cis-regulatory elements of the GLUT2 and insulin promoters. In particular, IB1 binds to the GTII cis-element of the GLUT2 and insulin genes (see U.S. Pat. No. 5,880,261). The IB proteins, and in particular, IB1 and IB2, are expressed predominantly in the brain and pancreas. Accordingly, the SH3-BPs of the invention are useful in specifically targeting the JNK signaling pathway in the brain and pancreas.

The intermediate kinase MKK7 of the three-kinase module binds to the highly conserved Src-homology 3 (SH3) domain regions contained in the IB1 and IB2 proteins. SH3 domains are small protein modules containing approximately 50 to 60 amino acid residues. These domains have been identified in a variety of intracellular signaling and membrane-associated polypeptides. The SH3 domain has been found to mediate protein-protein interactions that are involved in the coupling of intracellular signaling pathways, regulation of catalytic activity of proteins, recruitment of substrates to enzymes, and localization of proteins to a specific subcellular compartment. See Weng et al., Mol. and Cell. Biol. 15(10):5627-34 (1995).

The core, conserved binding motif of the SH3 domain is Pro-x-x-Pro (SEQ ID NO: 35). SH3 domains generally bind to proline-rich peptides, thereby forming an extended, left-hand helical conformation, known as the polyproline-2 (PPII) helix. See Mayer, J. Cell Sci. 114(7):1253-63 (2001).

The SH3 binding peptides of the invention were identified by panning a phage display library against GST-SH3$_{IB1/2}$ fusion proteins to characterize peptides that bind to the highly conserved SH3 domains of IB1 and IB2 (See, Example 1). SH3 binding peptides obtained from the biopanning experiment are shown in FIG. 1.

Sequence comparison between the sequences obtained from the phage display biopanning experiment, as shown in FIG. 1, revealed two conserved 6 amino acid sequence motifs SXSVGX (SEQ ID NO: 5) and PPSPRP (SEQ ID NO: 6). The latter sequence corresponds to the SH3 binding consensus sequence, PXXP (SEQ ID NO: 35), shown in FIG. 1.

The SH3 binding peptides of the invention can be used in any situation in which inhibition of JNK signaling is desired. This includes in vitro applications, ex vivo, and in vivo applications. As JNKs and all its isoforms participate in the development and establishment of pathological states or in pathways, the SH3 binding peptides can be used to prevent or inhibit the occurrence of such pathological states. This includes prevention, treatment and alleviation of symptoms of diseases and prevention, treatment and alleviation of symptoms of conditions secondary to therapeutic actions. The SH3-BPs of the invention are useful in treatment, prevention or alleviation of symptoms of pancreatic disorders, neurodegenerative diseases and apoptotic associated disorders of for example the pancreas and the brain. For example, the peptides of the present invention can be used to treat or prevent or alleviate a symptom of, e.g., pancreatic disorders such as diabetes, pancreatitis, or pancreatic cancer; neurodegenerative and neurological disorders such as Amyotrophic Lateral Sclerosis (ALS), Parkinson's disease, Huntington's disease, Alzheimer's disease, schizophrenia and stroke; ionizing radiation; immune responses (including autoimmune diseases); ischemia/reperfusion injuries; heart and cardiovascular hypertrophies; and some cancers (e.g., Bcr-Abl transformation).

The SH3-BPs are also used to inhibit expression of genes and gene products whose expression increases in the presence of an active JNK polypeptide, such as for example, proinflammatory cytokines. Proinflammatory cytokines are found in all forms of inflammatory, auto-inflammatory, immune and autoimmune diseases, degenerative diseases, myopathies, cardiomyopathies, and graft rejection.

The polynucleotides provided by the present invention are used to express recombinant peptides for analysis, characterization or therapeutic use; as markers for tissues in which the corresponding peptides is preferentially expressed (either constitutively or at a particular stage of tissue differentiation or development or in disease states). Other uses for the nucleic acids include, e.g., molecular weight markers in gel electrophoresis-based analysis of nucleic acids.

The SH3 binding peptides disclosed herein are presented in Table 1. The table presents the name of the SH3 binding peptide, as well as its sequence identifier number, length, and amino acid sequence. The abbreviation "RV", as used herein, refers to a "retro-inverso isomer" of a peptide.

TABLE 1

| PEPTIDE NAME | SEQ ID NO | AA | Sequence |
|---|---|---|---|
| αSH3 | 1 | 12 | SVSVGMPPSP RP |
| αSH3 (generic) | 2 | 12 | SX(S/P)V(G/L)XPPSP RP |
| TAT-αSH3 | 3 | 21 | RKKRRQRRRS VSVGMPPSPR P |
| TAT-αSH3 (generic) | 4 | 29 | XXXXRKKRRQ RRRXXXXSX(S/P) V(G/L)XPPSPRP |
| αSH3 binding motif 1 (generic) | 5 | 6 | SXSVGX |
| αSH3 binding motif 2 (generic) | 6 | 6 | PPSPRP |
| αSH3$_2$ | 7 | 12 | SVSVGMKPSP RP |
| αSH3$_3$ | 8 | 12 | SVSVGKNPSP RH |
| αSH3$_4$ | 9 | 12 | TQPMMAPPSP RQ |
| αSH3$_5$ | 10 | 12 | LDSLCHPQSP RP |
| αSH3$_6$ | 11 | 11 | HPFLVSSSPR P |
| αSH3$_7$ | 12 | 9 | GQPFFSPFS |
| αSH3$_8$ | 13 | 11 | PPSNLIPPTL R |
| αSH3$_9$ | 14 | 6 | SPPSNL |
| αSH3$_{10}$ | 15 | 11 | FNPWSSKPSL L |
| αSH3$_{11}$ | 16 | 12 | NASVGNDHSH SH |
| αSH3$_{12}$ | 17 | 11 | EHMALTYPFR P |
| RV-αSH3 | 18 | 12 | PRPSPPMGVS VS |
| RV-αSH3 (generic) | 19 | 12 | PRPSPPX(G/L)V(S/P) XS |
| RV-TAT-αSH3 | 20 | 21 | PRPSPPMGVS VSRRRQRRKK R |

TABLE 1-continued

| PEPTIDE NAME | SEQ ID NO | AA | Sequence |
|---|---|---|---|
| RV-TAT-αSH3 (generic) | 21 | 29 | PRPSPPX(G/L)V(S/P) XSXXXXRRRQ RRKKRXXXX |
| RV-αSH3 binding motif 1 (generic) | 22 | 6 | XGVSXS |
| RV-αSH3 binding motif 2 (generic) | 23 | 6 | PRPSPP |
| RV-αSH3$_2$ | 24 | 12 | PRPSPKMGVS VS |
| RV-αSH3$_3$ | 25 | 12 | HRPSPNKGVS VS |
| RV-αSH3$_4$ | 26 | 12 | QRPSPPAMMP QT |
| RV-αSH3$_5$ | 27 | 12 | PRPSQPHCLS DL |
| RV-αSH3$_6$ | 28 | 11 | PRPSSSVLFP H |
| RV-αSH3$_7$ | 29 | 9 | SFPSFFPQG |
| RV-αSH3$_8$ | 30 | 11 | RLTPPILNSP P |
| RV-αSH3$_9$ | 31 | 6 | LNSPPS |
| RV-αSH3$_{10}$ | 32 | 11 | LLSPKSSWPN F |
| RV-αSH3$_{11}$ | 33 | 12 | HSHSHDNGVS AN |
| RV-αSH3$_{12}$ | 34 | 11 | PRFPYTLAMH E |

SH3 Binding Peptides

In one aspect, the invention provides an SH3 binding peptide. Exemplary SH3 binding peptides include the amino acid sequences of SEQ ID NO: 1-35. No particular length is implied by the term "peptide." In some embodiments, the SH3 binding peptide is less than 500 amino acids in length, e.g., less than or equal to 450, 400, 350, 300, 250, 200, 150, 100, 75, 50, 35, or 25 amino acids in length. Preferably, the peptide is capable of transport across a biological membrane, e.g., a nuclear or cellular membrane. In various embodiment, the SH3 binding peptide includes the amino acid sequence of one or more of SEQ ID NO: 1-35. The SH3 binding peptides bind at least one IB protein, e.g., IB1 or IB2. Binding of at least one IB protein, e.g., IB1 or IB2, can be measured by methods known in the art, such as for example, by using an affinity binding assay having a GST-IB1 or GST-IB2 fusion protein as an affinity matrix. Alternatively, the peptide inhibits MKK7 binding to an SH3 domain polypeptide. Inhibition of MKK7 binding is measured by methods known in the art, for example using pull down experiments as described in Example 3. Inhibition of MKK7 binding is also measured by observing inhibition of JNK signaling, i.e., JNK activation. INK signaling is determined for example using a solid phase JNK assay as described herein (see e.g., Example 7) and in Bonny et al., Diabetes 50:77-82 (2001). The term "an SH3 domain polypeptide", as used herein, is meant to refer to a polypeptide that contains one or more SH3 domain consensus sequences. A SH3 consensus sequence as described by Pfam database entry pfam00018.6 includes the amino acid sequence PKVVALYDYQARE-SDELSFK-KGDIIIVLE-KSDD--GWWKGRLKGT--KEGLIPSNYVEPV (SEQ ID NO: 40). Exemplary, SH3 polypeptides include intracellular signaling proteins such as the Src, Abl, Csk and ZAP70 families of protein tyrosine kinases (e.g., GenBank Accession No. P12931, P00519, P41240 and P43403, respectively, incorporated herein by reference in their entirety); mammalian phosphatidylinositol-specific phospholipase C-γ-1 and C-γ-2 (e.g., GenBank Accession No. NP_002652 and NP_002651, respectively, incorporated herein by reference in their entirety); mammalian phosphatidylinositol 3-kinase regulatory p85 subunit (e.g., GenBank Accession No: A38748, incorporated herein by reference in its entirety); mammalian Ras GTPase-activating protein (GAP) (e.g., GenBank Accession No: BAA11230, incorporated herein by reference in its entirety); adaptor proteins that mediate binding of guanine nucleotide exchange factors to growth factor receptors such as vertebrate GRB2 (e.g., GenBank Accession No: P29354 and AAC72075, incorporated herein by reference in their entirety); and cytoskeletal proteins such as fodrin (e.g., GenBank Accession No. AAA51702, AAA52468 and AAB28324, incorporated herein by reference in their entirety) and yeast actin binding protein ABP-1 (e.g., GenBank Accession No. LLBY, incorporated herein by reference in its entirety).

Examples of SH3 binding peptides include a peptide which includes (in whole or in part) the sequences of SEQ ID NO: 1-35 as shown in Table 1. As used herein, X may be any amino acid. The single residue represented by (S/P) may be either Ser or Pro in the generic sequence. The single residue represented by (G/L) may be either Gly or Leu in the generic sequence.

The SH3 binding peptides can be polymers of L-amino acids, D-amino acids, or a combination of both. For example, in various embodiments, the peptides are D retro-inverso peptides. The term "retro-inverso isomer" refers to an isomer of a linear peptide in which the direction of the sequence is reversed, and the term "D-retro-inverso isomer" refers to an isomer of a linear peptide in which the direction of the sequence is reversed and the chirality of each amino acid residue is inverted. See, e.g., Jameson et al., *Nature*, 368, 744-746 (1994); Brady et al., Nature, 368, 692-693 (1994). The net result of combining D-enantiomers and reverse synthesis is that the positions of carbonyl and amino groups in each amide bond are exchanged, while the position of the side-chain groups at each alpha carbon is preserved. Unless specifically stated otherwise, it is presumed that any given L-amino acid sequence of the invention may be made into an D retro-inverso peptide by synthesizing a reverse of the sequence for the corresponding native L-amino acid sequence.

SH3 binding peptides may be obtained or produced by methods well-known in the art, e.g. chemical synthesis, genetic engineering methods as discussed below. For example, a peptide corresponding to a portion of an SH3 binding peptide including a desired region or domain, or that mediates the desired activity in vitro, may be synthesized by use of a peptide synthesizer.

A candidate SH3 binding peptide may also be analyzed by hydrophilicity analysis (see, e.g., Hopp and Woods, 1981. *Proc Natl Acad Sci USA* 78: 3824-3828) that can be utilized to identify the hydrophobic and hydrophilic regions of the peptides, thus aiding in the design of substrates for experimental manipulation, such as in binding experiments, antibody synthesis. Secondary structural analysis may also be performed to identify regions of an SH3 binding peptide that assume specific structural motifs. See e.g., Chou and Fasman, 1974. *Biochem* 13: 222-223. Manipulation, translation, secondary structure prediction, hydrophilicity and hydrophobicity profiles, open reading frame prediction and plotting, and determination of sequence homologies can be accomplished using computer software programs available in the art. Other methods of structural analysis including, e.g., X-ray crystallography (see, e.g., Engstrom, 1974. *Biochem Exp Biol* 11: 7-13); mass spectroscopy and gas chromatography (see, e.g., METHODS IN PROTEIN SCIENCE, 1997. J. Wiley and Sons, New York, N.Y.) and computer modeling (see, e.g., Fletterick and Zoller, eds., 1986. Computer Graphics and Molecular Modeling, In: CURRENT COMMUNICATIONS IN MOLECULAR BIOLOGY, Cold Spring Harbor Laboratory Press, Cold Spring Harbor, N.Y.) may also be employed.

The present invention additionally relates to nucleic acids that encode SH3 binding to peptides having L-form amino acids, e.g., those L-peptides indicated in Table 1, as well as the complements of these sequences. Nucleic acids encoding the SH3 binding peptides may be obtained by any method known in the art (e.g., by PCR amplification using synthetic primers hybridizable to the 3'- and 5'-termini of the sequence and/or by cloning from a cDNA or genomic library using an oligonucleotide sequence specific for the given gene sequence).

For recombinant expression of one or more SH3 binding peptides, the nucleic acid containing all or a portion of the nucleotide sequence encoding the peptide may be inserted into an appropriate expression vector (i.e., a vector that contains the necessary elements for the transcription and translation of the inserted peptide coding sequence). In some embodiments, the regulatory elements are heterologous (i.e., not the native gene promoter). Alternately, the necessary transcriptional and translational signals may also be supplied by the native promoter for the genes and/or their flanking regions.

A variety of host-vector systems may be utilized to express the peptide coding sequence(s). These include, but are not limited to: (i) mammalian cell systems that are infected with vaccinia virus, adenovirus, and the like; (ii) insect cell systems infected with baculovirus and the like; (iii) yeast containing yeast vectors or (iv) bacteria transformed with bacteriophage, DNA, plasmid DNA, or cosmid DNA. Depending upon the host-vector system utilized, any one of a number of suitable transcription and translation elements may be used.

Promoter/enhancer sequences within expression vectors may utilize plant, animal, insect, or fungus regulatory sequences, as provided in the invention. For example, promoter/enhancer elements can b used from yeast and other fungi (e.g., the GAL4 promoter, the alcohol dehydrogenase promoter, the phosphoglycerol kinase promoter, the alkaline phosphatase promoter). Alternatively, or in addition, they may include animal transcriptional control regions, e.g., (i) the insulin gene control region active within pancreatic β-cells (see, e.g., Hanahan, et al., 1985. *Nature* 315: 115-122); (ii) the immunoglobulin gene control region active within lymphoid cells (see, e.g., Grosschedl, et al., 1984. *Cell* 38: 647-658); (iii) the albumin gene control region active within liver (see, e.g., Pinckert, et al., 1987. *Genes and Dev* 1: 268-276; (iv) the myelin basic protein gene control region active within brain oligodendrocyte cells (see, e.g., Readhead, et al., 1987. *Cell* 48: 703-712); and (v) the gonadotropin-releasing hormone gene control region active within the hypothalamus (see, e.g., Mason, et al., 1986. *Science* 234: 1372-1378), and the like.

Expression vectors or their derivatives include, e.g. human or animal viruses (e.g., vaccinia virus or adenovirus); insect viruses (e.g., baculovirus); yeast vectors; bacteriophage vectors (e.g., lambda phage); plasmid vectors and cosmid vectors.

A host cell strain may be selected that modulates the expression of inserted sequences of interest, or modifies or processes expressed peptides encoded by the sequences in the specific manner desired. In addition, expression from certain promoters may be enhanced in the presence of certain inducers in a selected host strain; thus facilitating control of the expression of a genetically-engineered peptides. Moreover, different host cells possess characteristic and specific mechanisms for the translational and post-translational processing and modification (e.g., glycosylation, phosphorylation, and the like) of expressed peptides. Appropriate cell lines or host systems may thus be chosen to ensure the desired modification and processing of the foreign peptide is achieved. For example, peptide expression within a bacterial system can be used to produce an unglycosylated core peptide; whereas expression within mammalian cells ensures "native" glycosylation of a heterologous peptide.

Also included in the invention are derivatives, fragments, homologs, analogs and variants of SH3 binding peptides and nucleic acids encoding these peptides. For nucleic acids, derivatives, fragments, and analogs provided herein are defined as sequences of at least 6 (contiguous) nucleic acids, and which have a length sufficient to allow for specific hybridization. For amino acids, derivatives, fragments, and analogs provided herein are defined as sequences of at least 4 (contiguous) amino acids, a length sufficient to allow for specific recognition of an epitope.

The length of the fragments are less than the length of the corresponding full-length nucleic acid or polypeptide from which the SH3 binding peptide, or nucleic acid encoding same, is derived. Derivatives and analogs may be full length or other than full length, if the derivative or analog contains a modified nucleic acid or amino acid. Derivatives or analogs of the SH3 binding peptides include, e.g., molecules including regions that are substantially homologous to the peptides, in various embodiments, by at least about 30%, 50%, 70%, 80%, or 95%, 98%, or even 99%, identity over an amino acid sequence of identical size or when compared to an aligned sequence in which the alignment is done by a computer homology program known in the art. For example sequence identity can be measured using sequence analysis software (Sequence Analysis Software Package of the Genetics Computer Group, University of Wisconsin Biotechnology Center, 1710 University Avenue, Madison, Wis. 53705), with the default parameters therein.

In the case of polypeptide sequences, which are less than 100% identical to a reference sequence, the non-identical positions are preferably, but not necessarily, conservative substitutions for the reference sequence. Conservative substitutions typically include substitutions within the following groups: glycine and alanine; valine, isoleucine, and leucine; aspartic acid and glutamic acid; asparagine and glutamine; serine and threonine; lysine and arginine; and phenylalanine and tyrosine. Thus, included in the invention are peptides having mutated sequences such that they remain homologous, e.g. in sequence, in function, and in antigenic character or other function, with a protein having the corresponding parent sequence. Such mutations can, for example, be mutations involving conservative amino acid changes, e.g., changes between amino acids of broadly similar molecular properties. For example, interchanges within the aliphatic group alanine, valine, leucine and isoleucine can be considered as conservative. Sometimes substitution of glycine for one of these can also be considered conservative. Other conservative interchanges include those within the aliphatic group aspartate and glutamate; within the amide group asparagine and glutamine; within the hydroxyl group serine and threonine; within the aromatic group phenylalanine, tyrosine and tryptophan; within the basic group lysine, arginine and histidine; and within the sulfur-containing group methionine and cysteine. Sometimes substitution within the group methionine and leucine can also be considered conservative. Preferred conservative substitution groups are aspartate-glutamate; asparagine-glutamine; valine-leucine-isoleucine; alanine-valine; phenylalanine-tyrosine; and lysine-arginine.

Where a particular polypeptide is said to have a specific percent identity to a reference polypeptide of a defined length, the percent identity is relative to the reference peptide. Thus, a peptide that is 50% identical to a reference polypeptide that is 100 amino acids long can be a 50 amino acid polypeptide that is completely identical to a 50 amino acid long portion of the reference polypeptide. It might also be a 100 amino acid long polypeptide, which is 50% identical to the reference polypeptide over its entire length. Of course, other polypeptides will meet the same criteria.

The invention also encompasses allelic variants of the disclosed polynucleotides or peptides; that is, naturally-occurring alternative forms of the isolated polynucleotide that also encode peptides that are identical, homologous or related to that encoded by the polynucleotides. Alternatively, non-naturally occurring variants may be produced by mutagenesis techniques or by direct synthesis.

Species homologs of the disclosed polynucleotides and peptides are also provided by the present invention. "Variant" refers to a polynucleotide or polypeptide differing from the polynucleotide or polypeptide of the present invention, but retaining essential properties thereof. Generally, variants are overall closely similar, and in many regions, identical to the polynucleotide or polypeptide of the present invention. The variants may contain alterations in the coding regions, non-coding regions, or both.

In some embodiments, altered sequences include insertions such that the overall amino acid sequence is lengthened while the protein retains trafficking properties. Additionally, altered sequences may include random or designed internal deletions that shorten the overall amino acid sequence while the protein retains transport properties.

The altered sequences can additionally or alternatively be encoded by polynucleotides that hybridize under stringent conditions with the appropriate strand of the naturally-occurring polynucleotide encoding a polypeptide or peptide from which the SH3 binding peptide is derived. The variant peptide can be tested for IB-binding and modulation of JNK-mediated activity using the herein described assays. 'Stringent conditions' are sequence dependent and will be different in different circumstances. Generally, stringent conditions can be selected to be about 5° C. lower than the thermal melting point ($T_M$) for the specific sequence at a defined ionic strength and pH. The $T_M$ is the temperature (under defined ionic strength and pH) at which 50% of the target sequence hybridizes to a perfectly matched probe. Typically, stringent conditions will be those in which the salt concentration is at least about 0.02 molar at pH 7 and the temperature is at least about 60° C. As other factors may affect the stringency of hybridization (including, among others, base composition and size of the complementary strands), the presence of organic solvents and the extent of base mismatching, the combination of parameters is more important than the absolute measure of any one.

High stringency can include, e.g., Step 1: Filters containing DNA are pretreated for 8 hours to overnight at 65° C. in buffer composed of 6×SSC, 50 mM Tris-HCl (pH 7.5), 1 mM EDTA, 0.02% PVP, 0.02% Ficoll, 0.02% BSA, and 500 µg/ml denatured salmon sperm DNA. Step 2: Filters are hybridized for 48 hours at 65° C. in the above prehybridization mixture to which is added 100 mg/ml denatured salmon sperm DNA and 5-20×10$^6$ cpm of $^{32}$P-labeled probe. Step 3: Filters are washed for 1 hour at 37° C. in a solution containing 2×SSC, 0.01% PVP, 0.01% Ficoll, and 0.01% BSA. This is followed by a wash in 0.1×SSC at 50° C. for 45 minutes. Step 4: Filters are autoradiographed. Other conditions of high stringency that may be used are well known in the art. See, e.g., Ausubel et al., (eds.), 1993, CURRENT PROTOCOLS IN MOLECULAR BIOLOGY, John Wiley and Sons, NY; and Kriegler, 1990, GENE TRANSFER AND EXPRESSION, A LABORATORY MANUAL, Stockton Press, NY.

Moderate stringency conditions can include the following: Step 1: Filters containing DNA are pretreated for 6 hours at 55° C. in a solution containing 6×SSC, 5×Denhardt's solution, 0.5% SDS and 100 mg/ml denatured salmon sperm DNA. Step 2: Filters are hybridized for 18-20 hours at 55° C. in the same solution with 5-20×106 cpm $^{32}$P-labeled probe added. Step 3: Filters are washed at 37° C. for 1 hour in a solution containing 2×SSC, 0.1% SDS, then washed twice for 30 minutes at 60° C. in a solution containing 1×SSC and 0.1% SDS. Step 4: Filters are blotted dry and exposed for autoradiography. Other conditions of moderate stringency that may be used are well-known in the art. See, e.g., Ausubel et al., (eds.), 1993, CURRENT PROTOCOLS IN MOLECULAR BIOLOGY, John Wiley and Sons, NY; and Kriegler, 1990, GENE TRANSFER AND EXPRESSION, A LABORATORY MANUAL, Stockton Press, NY.

Low stringency can include: Step 1: Filters containing DNA are pretreated for 6 hours at 40° C. in a solution containing 35% formamide, 5×SSC, 50 mM Tris-HCl (pH 7.5), 5 mM EDTA, 0.1% PVP, 0.1% Ficoll, 1% BSA, and 500 µg/ml denatured salmon sperm DNA. Step 2: Filters are hybridized for 18-20 hours at 40° C. in the same solution with the addition of 0.02% PVP, 0.02% Ficoll, 0.2% BSA, 100 µg/ml salmon sperm DNA, 10% (wt/vol) dextran sulfate, and 5-20× 106 cpm $^{32}$P-labeled probe. Step 3: Filters are washed for 1.5 hours at 55° C. in a solution containing 2×SSC, 25 mM Tris-HCl (pH 7.4), 5 mM EDTA, and 0.1% SDS. The wash solution is replaced with fresh solution and incubated an additional 1.5 hours at 60° C. Step 4: Filters are blotted dry and exposed for autoradiography. If necessary, filters are washed for a third time at 65-68° C. and reexposed to film. Other conditions of low stringency that may be used are well known in the art (e.g., as employed for cross-species hybridizations). See, e.g., Ausubel et al., (eds.), 1993, CURRENT PROTOCOLS IN MOLECULAR BIOLOGY, John Wiley and Sons, NY; and Kriegler, 1990, GENE TRANSFER AND EXPRESSION, A LABORATORY MANUAL, Stockton Press, NY.

Chimeric Peptides Including an SH3 Binding Domain and a Trafficking Domain

In another aspect the invention provides a chimeric peptide that includes a first and second domain. The first domain includes a trafficking sequence, while the second domain includes an SH3 binding peptide linked by a covalent bond, e.g. peptide bond, to the first domain. The first and second domains can occur in any order in the peptide, and the peptide can include one or more of each domain.

A trafficking sequence is any sequence of amino acids that directs a peptide in which it is present to a desired cellular destination. Thus, the trafficking sequence can direct the peptide across the plasma membrane, e.g., from outside the cell, through the plasma membrane, and into the cytoplasm. Alternatively, or in addition, the trafficking sequence can direct the peptide to a desired location within the cell, e.g., the nucleus, the ribosome, the ER, a lysosome, or peroxisome.

In some embodiments, the trafficking peptide is derived from a known membrane-translocating sequence. For example, the trafficking peptide may include sequences from the human immunodeficiency virus (HIV)1 TAT protein. This protein is described in, e.g., U.S. Pat. Nos. 5,804,604 and 5,674,980, each incorporated herein by reference. The SH3 binding peptide may be linked to some or all of the entire 86 amino acids that make up the TAT protein. For example, a functionally effective fragment or portion of a TAT protein that has fewer than 86 amino acids, which exhibits uptake into cells, and optionally uptake into the cell nucleus, can be used. In one embodiment, the fragment includes a peptide containing TAT residues 49-57, e.g. NH$_2$-RKKRRQRRR-COOH (SEQ ID NO: 36) or a generic TAT sequence NH$_2$-X$_n$-RKKRRQRRR-X$_n$-COOH (SEQ ID NO: 37). A TAT peptide that includes the region that mediates entry and uptake into cells can be further defined using known techniques. See, e.g., Franked et al., *Proc. Natl. Acad Sci, USA* 86: 7397-7401 (1989).

The TAT sequence may be linked either to the N-terminal or the C-terminal end of the SH3 binding peptide. A hinge of two proline residues may be added between the TAT and SH3 binding peptide to create the full fusion peptide. For example, amino acid fusion peptides may be the TAT-αSH3 peptide (SEQ ID NO: 3) or the generic TAT-αSH3 peptide (SEQ ID NO: 4). Retro-inverso fusion peptides may be the RV-TAT-αSH3 peptide (SEQ ID NO: 20) or the generic RV-TAT-αSH3 peptide (SEQ ID NO: 21). The TAT peptide may be a retro-inverso peptide having the sequence NH$_2$-X$_n$-RRQRRKKR-X$_n$-COOH (SEQ ID NO: 38) or the TAT-peptide can be a generic retro-inverso peptide having the sequence NH$_2$-X$_n$-RRRQR-RKKR-X$_n$-COOH (SEQ ID NO: 39). In SEQ ID NO: 3-4 and 38-39, the number of "X" residues is not limited to the one depicted nor is the number of Xs in a given peptide limited to the one depicted, and accordingly, the "X" residues may vary as described above. The fusion peptide can include one or more of the SH3-BPs of SEQ ID NO: 1-35. For example, the fusion peptide can be a chimeric peptide comprising the sequence of SEQ ID NO: 36 covalently linked to the sequence of SEQ ID NO: 7, or alternatively the chimeric peptide can comprise the sequence of SEQ ID NO: 38 covalently linked to the sequence of SEQ ID NO: 24. For example, the fusion peptide can include a chimeric peptide comprising the sequence of SEQ ID NO: 36 covalently linked to a sequence selected from SEQ ID NO: 7-17, or alternatively, the chimeric peptide can comprise the sequence of SEQ ID NO: 38 covalently linked to an amino acid sequence selected from the group consisting of SEQ ID NO: 24-34. Any combination of SH3 binding peptides and trafficking sequences are within the scope of the present invention.

The fusion peptide can also include a peptide comprising the amino acid sequence of SEQ ID NO: 36 covalently linked to a peptide that includes an SXSVGX (SEQ ID NO: 5) motif and a PPSPRP (SEQ ID NO: 6) motif. Alternatively, the fusion peptide may be a chimeric peptide that includes the amino acid sequence of SEQ ID NO: 38 covalently linked to a peptide containing an XGVSXS (SEQ ID NO: 22) and a PRPSPP (SEQ ID NO: 23) motif. In one embodiment, the fusion peptide has a length that is less than 50 amino acids.

The trafficking sequence can be a single (i.e., continuous) amino acid sequence present in the TAT sequence. Alternatively it can be two or more amino acid sequences, which are present in TAT protein, but in the naturally-occurring protein are separated by other amino acid sequences. As used herein, TAT protein includes a naturally-occurring amino acid sequence that is the same as that of naturally-occurring TAT protein, or its functional equivalent protein or functionally equivalent fragments thereof (peptides). Such functional equivalent proteins or functionally equivalent fragments possess uptake activity into the cell and into the cell nucleus that is substantially similar to that of naturally-occurring TAT protein. TAT protein can be obtained from naturally-occurring sources or can be produced using genetic engineering techniques or chemical synthesis.

The amino acid sequence of naturally-occurring HIV TAT protein can be modified, for example, by addition, deletion and/or substitution of at least one amino acid present in the naturally-occurring TAT protein, to produce modified TAT protein (also referred to herein as TAT protein). Modified TAT protein or TAT peptide analogs with increased or decreased stability can be produced using known techniques. In some embodiments TAT proteins or peptides include amino acid sequences that are substantially similar, although not identical, to that of naturally-occurring TAT protein or portions thereof. In addition, cholesterol or other lipid derivatives can be added to TAT protein to produce a modified TAT having increased membrane solubility.

Variants of the TAT protein can be designed to modulate intracellular localization of TAT-SH3 binding peptide. When added exogenously, such variants are designed such that the ability of TAT to enter cells is retained (i.e., the uptake of the variant TAT protein or peptide into the cell is substantially similar to that of naturally-occurring HIV TAT). For example, alteration of the basic region thought to be important for nuclear localization (see, e.g., Dang and Lee, *J. Biol. Chem.* 264: 18019-18023 (1989); Hauber et al., *J. Virol.* 63: 1181-1187 (1989); Ruben et al., *J. Virol.* 63: 1-8 (1989)) can result in a cytoplasmic location or partially cytoplasmic location of TAT, and therefore, of the SH3 binding peptide. Alternatively, a sequence for binding a cytoplasmic or any other component or compartment (e.g., endoplasmic reticule, mitochondria, gloom apparatus, lysosomal vesicles,) can be introduced into TAT in order to retain TAT and the SH3 binding peptide in the cytoplasm or any other compartment to confer regulation upon uptake of TAT and the SH3 binding peptide.

Other sources for the trafficking peptide are well known in the art. For example, VP22 (described in, e.g., WO 97/05265; Elliott and O'Hare, *Cell* 88: 223-233 (1997)), or non-viral proteins (Jackson et al., *Proc. Natl. Acad. Sci. USA* 89: 10691-10695 (1992)). Other suitable trafficking peptides include peptides derived from the *Drosophila melanogaster* antennapedia (Antp) homeotic transcription factor, the h region of the signal sequence of Kaposi fibroblast growth factor (MTS), and the protein PreS2 of hepatitis B virus (HBV) (Kelemen, et al., J. Biol. Chem. 277(10):8741-8748 (2002)). Alternatively, the trafficking peptide is a polymer of cationic macromolecules or an arginine-rich peptide including a poly-arginine repeat.

The SH3 binding peptide and the trafficking sequence can be linked by chemical coupling in any suitable manner known in the art. Many known chemical cross-linking methods are non-specific, i.e.; they do not direct the point of coupling to any particular site on the transport polypeptide or cargo macromolecule. As a result, use of non-specific cross-linking agents may attack functional sites or sterically block active sites, rendering the conjugated proteins biologically inactive.

One way to increasing coupling specificity is to directly chemical coupling to a functional group found only once or a few times in one or both of the polypeptides to be cross-linked. For example, in many proteins, cysteine, which is the only protein amino acid containing a thiol group, occurs only a few times. Also, for example, if a polypeptide contains no lysine residues, a cross-linking reagent specific for primary amines will be selective for the amino terminus of that polypeptide. Successful utilization of this approach to increase coupling specificity requires that the polypeptide have the suitably rare and reactive residues in areas of the molecule that may be altered without loss of the molecule's biological activity.

Cysteine residues may be replaced when they occur in parts of a polypeptide sequence where their participation in a cross-linking reaction would otherwise likely interfere with biological activity. When a cysteine residue is replaced, it is typically desirable to minimize resulting changes in polypeptide folding. Changes in polypeptide folding are minimized when the replacement is chemically and sterically similar to cysteine. For these reasons, serine is preferred as a replacement for cysteine. As demonstrated in the examples below, a cysteine residue may be introduced into a polypeptide's amino acid sequence for cross-linking purposes. When a cysteine residue is introduced, introduction at or near the amino or carboxy terminus is preferred. Conventional methods are available for such amino acid sequence modifications, whether the polypeptide of interest is produced by chemical synthesis or expression of recombinant DNA.

Coupling of the two constituents can be accomplished via a coupling or conjugating agent. There are several intermolecular cross-linking reagents which can be utilized, See for example, Means and Feeney, Chemical Modification of Proteins, Holden-Day, 1974, pp. 39-43. Among these reagents are, for example, J-succinimidyl 3-(2-pyridyldithio) propionate (SPDP) or N,N'-(1,3-phenylene) bismaleimide (both of which are highly specific for sulfhydryl groups and form irreversible linkages); N,N'-ethylene-bis-(iodoacetamide) or other such reagent having 6 to 11 carbon methylene bridges (which relatively specific for sulfhydryl groups); and 1,5-difluoro-2,4-dinitrobenzene (which forms irreversible linkages with amino and tyrosine groups). Other cross-linking reagents useful for this purpose include: p,p'-difluoro-m,m'-dinitrodiphenylsulfone (which forms irreversible cross-linkages with amino and phenolic groups); dimethyl adipimidate (which is specific for amino groups); phenol-1,4-disulfonylchloride (which reacts principally with amino groups); hexamethylenediisocyanate or diisothiocyanate, or azophenyl-p-diisocyanate (which reacts principally with amino groups); glutaraldehyde (which reacts with several different side chains) and disdiazobenzidine (which reacts primarily with tyrosine and histidine).

Cross-linking reagents may be homobifunctional, i.e., having two functional groups that undergo the same reaction. A preferred homobifunctional cross-linking reagent is bismaleimidohexane ("BMH"). BMH contains two maleimide functional groups, which react specifically with sulfhydryl-containing compounds under mild conditions (pH 6.5-7.7). The two maleimide groups are connected by a hydrocarbon chain. Therefore, BMH is useful for irreversible cross-linking of polypeptides that contain cysteine residues.

Cross-linking reagents may also be heterobifunctional. Heterobifunctional cross-linking agents have two different functional groups, for example an amine-reactive group and a thiol-reactive group, that will cross-link two proteins having free amines and thiols, respectively. Examples of heterobifunctional cross-linking agents are succinimidyl 4-(N-maleimidomethyl)cyclohexane-1-carboxylate ("SMCC"), m-maleimidobenzoyl-N-hydroxysuccinimide ester ("MBS"), and succinimide 4-(p-maleimidophenyl) butyrate ("SMPB"), an extended chain analog of MBS. The succinimidyl group of these cross-linkers reacts with a primary amine, and the thiol-reactive maleimide forms a covalent bond with the thiol of a cysteine residue.

Cross-linking reagents often have low solubility in water. A hydrophilic moiety, such as a sulfonate group, may be added to the cross-linking reagent to improve its water solubility. Sulfo-MBS and sulfo-SMCC are examples of cross-linking reagents modified for water solubility.

Many cross-linking reagents yield a conjugate that is essentially non-cleavable under cellular conditions. However, some cross-linking reagents contain a covalent bond, such as a disulfide, that is cleavable under cellular conditions. For example, Traut's reagent, dithiobis (succinimidylpropionate) ("DSP"), and N-succinimidyl 3-(2-pyridyldithio) propionate ("SPDP") are well-known cleavable cross-linkers. The use of a cleavable cross-linking reagent permits the cargo moiety to separate from the transport polypeptide after delivery into the target cell. Direct disulfide linkage may also be useful.

Numerous cross-linking reagents, including the ones discussed above, are commercially available. Detailed instructions for their use are readily available from the commercial suppliers. A general reference on protein cross-linking and conjugate preparation is: Wong, CHEMISTRY OF PROTEIN CONJUGATION AND CROSS-LINKING, CRC Press (1991).

Chemical cross-linking may include the use of spacer arms. Spacer arms provide intramolecular flexibility or adjust intramolecular distances between conjugated moieties and thereby may help preserve biological activity. A spacer arm may be in the form of a polypeptide moiety that includes spacer amino acids, e.g. proline. Alternatively, a spacer arm may be part of the cross-linking reagent, such as in "long-chain SPDP" (Pierce Chem. Co., Rockford, Ill., cat. No. 21651H).

Alternatively, the chimeric peptide can be produced as a fusion peptide that includes the trafficking sequence and the SH3 binding peptide which can conveniently be expressed in known suitable host cells. Fusion peptides, as described herein, can be formed and used in ways analogous to or readily adaptable from standard recombinant DNA techniques, as describe above.

Production of Antibodies Specific for SH3 Binding Peptides

SH3 binding peptides, including chimeric peptides including the SH3 binding peptides (e.g., peptides including the amino acid sequences shown in Table 1), as well peptides, or derivatives, fragments, analogs or homologs thereof, may be utilized as immunogens to generate antibodies that immunospecifically-bind these peptide components. Such antibodies include, e.g., polyclonal, monoclonal, chimeric, single chain, Fab fragments and a Fab expression library. In a specific embodiment, antibodies to human peptides are disclosed. In another specific embodiment, fragments of the SH3 binding peptides are used as immunogens for antibody production. Various procedures known within the art may be used for the production of polyclonal or monoclonal antibodies to an SH3 binding peptide, or derivative, fragment, analog or homolog thereof.

For the production of polyclonal antibodies, various host animals may be immunized by injection with the native peptide, or a synthetic variant thereof, or a derivative of the foregoing. Various adjuvants may be used to increase the immunological response and include, but are not limited to, Freund's (complete and incomplete), mineral gels (e.g., aluminum hydroxide), surface active substances (e.g., lysolecithin, pluronic polyols, polyanions, peptides, oil emulsions, dinitrophenol, etc.) and human adjuvants such as *Bacille Calmette-Guerin* and *Corynebacterium parvum*.

For preparation of monoclonal antibodies directed towards an SH3 binding peptide, or derivatives, fragments, analogs or homologs thereof, any technique that provides for the production of antibody molecules by continuous cell line culture may be utilized. Such techniques include, but are not limited to, the hybridoma technique (see, Kohler and Milstein, 1975. *Nature* 256: 495-497); the trioma technique; the human B-cell hybridoma technique (see, Kozbor, et al., 1983. *Immunol Today* 4: 72) and the EBV hybridoma technique to produce human monoclonal antibodies (see, Cole, et al., 1985. In: *Monoclonal Antibodies and Cancer Therapy*, Alan R. Liss, Inc., pp. 77-96). Human monoclonal antibodies may be utilized in the practice of the present invention and may be produced by the use of human hybridomas (see, Cote, et al., 1983. *Proc Natl Acad Sci USA* 80: 2026-2030) or by transforming human B-cells with Epstein Barr Virus in vitro (see, Cole, et al., 1985. In: *Monoclonal Antibodies and Cancer Therapy* (Alan R. Liss, Inc., pp. 77-96).

According to the invention, techniques can be adapted for the production of single-chain antibodies specific to an SH3 binding peptide (see, e.g., U.S. Pat. No. 4,946,778). In addition, methodologies can be adapted for the construction of Fab expression libraries (see, e.g., Huse, et al., 1989. *Science* 246: 1275-1281) to allow rapid and effective identification of monoclonal Fab fragments with the desired specificity for an SH3 binding peptide or derivatives, fragments, analogs or homologs thereof. Non-human antibodies can be "humanized" by techniques well known in the art. See e.g., U.S. Pat. No. 5,225,539. Antibody fragments that contain the idiotypes to an SH3 binding peptide may be produced by techniques known in the art including, e.g., (i) an $F(ab)_2$ fragment produced by pepsin digestion of an antibody molecule; (ii) an Fab fragment generated by reducing the disulfide bridges of an $F(ab')_2$ fragment; (iii) an Fab fragment generated by the treatment of the antibody molecule with papain and a reducing agent and (iv) Fv fragments.

In one embodiment, methodologies for the screening of antibodies that possess the desired specificity include, but are not limited to, enzyme-linked immunosorbent assay (ELISA) and other immunologically-mediated techniques known within the art. In a specific embodiment, selection of antibodies that are specific to a particular domain of an SH3 binding peptide is facilitated by generation of hybridomas that bind to the fragment of an SH3 binding peptide possessing such a domain. Antibodies that are specific for a domain within an SH3 binding peptide, or derivative, fragments, analogs or homologs thereof, are also provided herein.

The anti-SH3 binding peptide antibodies may be used in methods known within the art relating to the localization and/or quantitation of an SH3 binding peptide (e.g., for use in measuring levels of the peptide within appropriate physiological samples, for use in diagnostic methods, for use in imaging the peptide, and the like). In a given embodiment, antibodies for the SH3 binding peptides, or derivatives, fragments, analogs or homologs thereof that contain the antibody derived binding domain, are utilized as pharmacologically active compounds (hereinafter "Therapeutics").

Methods of Inhibiting Apoptosis

Also included in the invention are methods for inhibiting apoptosis in a cell, treating an apoptosis-associated disorder or alleviating a symptom of an apoptosis-associated disorder in a subject. Apoptosis, also known as programmed cell death, plays a role in development, aging and in various pathologic conditions.

An apoptosis associated disorder includes for example, immunodeficiency diseases, including AIDS/HIV, senescence, pancreatic disorders such as diabetes (i.e., Type I or Type II), pancreatitis, and pancreatic cancer, neurological disorders (e.g., neurodegenerative diseases such as Amyotrophic Lateral Sclerosis, Parkinson's disease, Huntington's disease, Alzheimer's disease, and stroke, any degenerative disorder, schizophrenia, ischemic and reperfusion cell death, acute ischemic injury, infertility, wound-healing, and the like.

Neurodegenerative diseases are characterized by gradual progressive neuronal cell death. Other neurological disorders include neuropathy, e.g., diabetic neuropathy, encephalitis and meningitis. Neurological disorders are diagnosed, typically by a physician using standard methodologies known be those skilled in the art. Such methods include, neurologic history, neurological examination. Neurological examination is accomplished by a systematic physical examination of all functions of the cerebrum, peripheral nerves and muscle. Diagnosis is also made using techniques for imaging the nervous system with such as computed tomography, magnetic resonance imaging, myelography, and positron emission tomography.

Some pancreatic disorders, e.g., diabetes or pancreatitis are characterized by gradual progressive pancreatic cell death. For example, in diabetes, insulin producing cells (e.g., β-cells) are destroyed resulting in an insulin deficiency. In pancreatitis, local and systemic inflammation results in the release of cytokines which lead to pancreatic cell death. Pancreatic disorders are diagnosed, typically by a physician using standard methodologies known be those skilled in the art. Such methods include elevated of serum amylase and lipase levels, hyperglycemia, hypocalcemia, or hyperbilirubinemia.

A symptom associated with an apoptosis-associated disorder is meant to include any sensation or change in bodily function experienced by a patient that is associated with a particular disease. For example, in diabetes, a symptom associated with the disorder includes low serum insulin levels, high serum glucose, pancreatic β-cell death, neuropathy, and ketoacidosis. Alternatively, in a neurodegenerative disorder, a symptom includes, for example, neuronal cell death, neuron degeneration, neuron dysfunction, cerebral atrophy, accumulation of amyloid plaques in the brain, and accumulation of filamentous structures (e.g., Lewy bodies, tau-rich intraneuronal neurofibrillary tangles (NFTs)).

Many methods for measuring apoptosis, including those described herein, are known to the skilled artisan including, but not limited to, the classic methods of DNA ladder formation by gel electrophoresis and of morphologic examination by electron microscopy. The more recent and readily used method for measuring apoptosis is flow cytometry. Flow cytometry permits rapid and quantitative measurements on apoptotic cells. Many different flow cytometric methods for the assessment of apoptosis in cells have been described (Darzynkiewicz et al. *Cytometry* 13: 795-808, 1992). Most of these methods measure to 0 apoptotic changes in cells by staining with various DNA dyes (i.e. propidium iodide (PI), DAPI, Hoechst 33342), however, techniques using the terminal deoxynucleotidyl transferase (TUNNEL) or nick translation assays have also been developed (Gorczyca et al. Cancer Res 53: 1945-1951, 1993). Recently, rapid flow cytometric staining methods that use Annexin V for detection of phosphatidylserine exposure on the cell surface as a marker of apoptosis have become commercially available.

Apoptosis is inhibited in a cell by contacting a cell with an SH3 binding peptide, an SH3 chimeric peptide, or nucleic acid encoding an SH3 binding peptide in an amount sufficient to inhibit apoptosis. For example the cell is contacted with any one of SEQ ID NO: 1-35. The cell is a pancreatic cell, e.g., a pancreatic n-cell or a neuronal cell. The cell population that is exposed to, i.e., contacted with, the SH3 binding peptide can be any number of cells, i.e., one or more cells, and can be provided in vitro, in vivo, or ex vivo.

For example, to determine whether a compound inhibits cell death, a compound is tested by incubating the compound with a primary or immortalized cell, inducing a state of oxidative stress of the cells (e.g., by incubating them with $H_2O_2$) and measuring cell viability by standard methods. As a control the cells are incubated in the absence if the compound and then the treated cells are incubated in the absence of the compound and then treated to induce a state of oxidative stress. A decrease in cell death (or an increase in the number of viable cells) in the compound treated sample indicates that the compound inhibits oxidative-stress induced cell death, i.e., apoptosis. The test is repeated using different does of the compound to determine the dose range in which the compound functions to inhibit apoptosis.

An apoptosis-associated disorder is treated or a symptom of apoptosis is alleviated in a subject by administering to a subject in need thereof a biologically-active therapeutic compound (hereinafter "Therapeutic").

The Therapeutics include, e.g.: (i) any one or more of the SH3 binding peptides or SH3 chimeric peptides, and derivative, fragments, analogs and homologs thereof; (ii) antibodies directed against the SH3 binding peptides; (iii) nucleic acids encoding an SH3 binding peptide or SH3 chimeric peptide, and derivatives, fragments, analogs and homologs thereof; (iv) antisense nucleic acids to sequences encoding an SH3 binding peptide, and (v) modulators (i.e., inhibitors, agonists and antagonists). For example, the therapeutic includes to SEQ ID NO: 1-35.

The term "therapeutically effective" means that the amount of SH3-BP, for example, which is used, is of sufficient quantity to ameliorate the apoptosis associated disorder.

The subject is e.g., any mammal, e.g., a human, a primate, mouse, rat, dog, cat, cow, horse, pig.

Also included in the invention also are methods of treating cell-proliferative disorders associated with INK activation. The term "cell-proliferative disorder" denotes malignant as well as non-malignant cell populations that often appear to differ morphologically and functionally from the surrounding tissue. For example, the method may be useful in treating malignancies of the various organ systems, in which activation of JNK has often been demonstrated, e.g., lung, breast, lymphoid, gastrointestinal, and genito-urinary tract as well as adenocarcinomas which include malignancies such as most colon cancers, renal-cell carcinoma, prostate cancer, non-small cell carcinoma of the lung, cancer of the small intestine and cancer of the esophagus. Cancers with Bcr-Abl oncogenic transformations that clearly require activation of JNK are also included. Essentially, any disorder, which is etiologically linked to INK kinase activity, would be considered susceptible to treatment.

Methods of Promoting Neuronal Cell Growth and Regeneration

Also included in the invention are methods promoting (i.e., increasing) neuronal cell growth or regeneration by contacting a cell with a SH3 binding peptide, chimeric peptide or nucleic acid of the invention. For example, the cell is contacted with the peptide of SEQ ID NO: 1-35.

A neuronal cell is any cell derived from the central or peripheral nervous system, e.g., neuron, neurite or dendrite. The cell population that is exposed to, i.e., contacted with, the SH3 binding peptide, fusion peptide or nucleic acid of the invention can be any number of cells, i.e., one or more cells, and can be provided in vitro, in vivo, or ex vivo. When the cell is provided in vivo or ex vivo, the subject may be any mammal, e.g., a human, a primate, mouse, rat, dog, cat, cow, horse, pig.

Many methods for measuring neuronal cell growth, are known to the skilled artisan including, but not limited to, measuring cell viability.

For example, to determine whether a compound promotes neuronal cell growth or regeneration, a compound is tested by incubating the compound with a primary or immortalized neuronal cell inducing a state of stress of the cells (e.g., by incubating them with $H_2O_2$ or NMDA, as described herein) and measuring cell viability. As a control the cells are incubated in the absence if the compound and then the treated cells are incubated in the absence of the compound and then treated to induce a state of stress. A decrease in cell death (or an increase in the number of viable cells) in the compound treated sample indicates that the compound promotes cell growth or regeneration.

Pharmaceutical Compositions

The SH3 binding peptides, fusion peptides and nucleic acids of the invention can be formulated in pharmaceutical compositions. These compositions may comprise, in addition to one of the above substances, a pharmaceutically acceptable excipient, carrier, buffer, stabilizer or other materials well known to those skilled in the art. Such materials should be non-toxic and should not interfere with the efficacy of the active ingredient. The precise nature of the carrier or other material may depend on the route of administration, e.g. oral, intravenous, cutaneous or subcutaneous, nasal, intramuscular, intraperitoneal or patch routes.

Pharmaceutical compositions for oral administration may be in tablet, capsule, powder or liquid form. A tablet may include a solid carrier such as gelatin or an adjuvant. Liquid pharmaceutical compositions generally include a liquid carrier such as water, petroleum, animal or vegetable oils, mineral oil or synthetic oil. Physiological saline solution, dextrose or other saccharide solution or glycols such as ethylene glycol, propylene glycol or polyethylene glycol may be included.

For intravenous, cutaneous or subcutaneous injection, or injection at the site of affliction, the active ingredient will be in the form of a parenterally acceptable aqueous solution which is pyrogen-free and has suitable pH, isotonicity and stability. Those of relevant skill in the art are well able to prepare suitable solutions using, for example, isotonic vehicles such as Sodium Chloride Injection, Ringer's Injection, Lactated Ringer's Injection. Preservatives, stabilizers, buffers, antioxidants and/or other additives may be included, as required.

Whether it is a polypeptide, peptide, or nucleic acid molecule, other pharmaceutically useful compound according to the present invention that is to be given to an individual, administration is preferably in a "prophylactically effective amount" or a "therapeutically effective amount" (as the case may be, although prophylaxis may be considered therapy), this being sufficient to show benefit to the individual. The actual amount administered, and rate and time-course of administration, will depend on the nature and severity of what is being treated. Prescription of treatment, e.g. decisions on dosage etc, is within the responsibility of general practitioners and other medical doctors, and typically takes account of the disorder to be treated, the condition of the individual patient, the site of delivery, the method of administration and other factors known to practitioners. Examples of the techniques and protocols mentioned above can be found in REMINGTON'S PHARMACEUTICAL SCIENCES, 16th edition, Osol, A. (ed), 1980.

Alternatively, targeting therapies may be used to deliver the active agent more specifically to certain types of cell, by the use of targeting systems such as antibody or cell specific ligands. Targeting may be desirable for a variety of reasons; for example if the agent is unacceptably toxic, or if it would otherwise requite too high a dosage, or if it would not otherwise be able to enter the target cells.

Instead of administering these agents directly, they could be produced in the target cells by expression from an encoding gene introduced into the cells, e.g. in a viral vector (a variant of the VDEPT technique—see below). The vector could be targeted to the specific cells to be treated, or it could contain regulatory elements, which are switched on more or less selectively by the target cells.

Alternatively, the agent could be administered in a precursor form, for conversion to the active form by an activating agent produced in, or targeted to, the cells to be treated. This type of approach is sometimes known as ADEPT or VDEPT; the former involving targeting the activating agent to the cells by conjugation to a cell-specific antibody, while the latter involves producing the activating agent, e.g. an SH3 binding peptide, in a vector by expression from encoding DNA in a viral vector (see for example, EP-A-415731 and WO 90/07936).

In a specific embodiment of the present invention, nucleic acids include a sequence that encodes an SH3 binding peptide, or functional derivatives thereof, are administered to modulate activated JNK signaling pathways by way of gene therapy. In more specific embodiments, a nucleic acid or nucleic acids encoding an SH3 binding peptide, or functional to derivatives thereof, are administered by way of gene therapy. Gene therapy refers to therapy that is performed by the administration of a specific nucleic acid to a subject. In this embodiment of the present invention, the nucleic acid produces its encoded peptide(s), which then serve to exert a therapeutic effect by modulating function of the disease or disorder. Any of the methodologies relating to gene therapy available within the art may be used in the practice of the present invention. See e.g., Goldspiel, et at, 1993. *Clin Pharm* 12: 488-505.

In a preferred embodiment, the Therapeutic comprises a nucleic acid that is part of an expression vector expressing any one or more of the αSH3-related peptides, or fragments, derivatives or analogs thereof, within a suitable host. In a specific embodiment, such a nucleic acid possesses a promoter that is operably-linked to coding region(s) of an SH3 binding peptide. The promoter may be inducible or constitutive, and, optionally, tissue-specific. In another specific embodiment, a nucleic acid molecule is used in which coding sequences (and any other desired sequences) are flanked by regions that promote homologous recombination at a desired site within the genome, thus providing for intra-chromosomal expression of nucleic acids. See e.g., Koller and Smithies, 1989. *Proc Natl Acad Sci USA* 86: 8932-8935.

Delivery of the Therapeutic nucleic acid into a patient may be either direct (i.e., the patient is directly exposed to the nucleic acid or nucleic acid-containing vector) or indirect (i.e., cells are first transformed with the nucleic acid in vitro, then transplanted into the patient). These two approaches are known, respectively, as in vivo or ex vivo gene therapy. In a specific embodiment of the present invention, a nucleic acid is directly administered in vivo, where it is expressed to produce the encoded product. This may be accomplished by any of numerous methods known in the art including, e.g., constructing the nucleic acid as part of an appropriate nucleic acid expression vector and administering the same in a manner such that it becomes intracellular (e.g., by infection using a defective or attenuated retroviral or other viral vector; see U.S. Pat. No. 4,980,286); directly injecting naked DNA; using microparticle bombardment (e.g., a "Gene Gun®; Biolistic, DuPont); coating the nucleic acids with lipids; using associated cell-surface receptors/transfecting agents; encapsulating in liposomes, microparticles, or microcapsules; administering it in linkage to a peptide that is known to enter the nucleus; or by administering it in linkage to a ligand predisposed to receptor-mediated endocytosis (see, e.g., Wu and Wu, 1987. *J Biol Chem* 262: 4429-4432), which can be used to "target" cell types that specifically express the receptors of interest, etc.

An additional approach to gene therapy in the practice of the present invention involves transferring a gene into cells in in vitro tissue culture by such methods as electroporation, lipofection, calcium phosphate-mediated transfection, viral infection, or the like. Generally, the method of transfer includes the concomitant transfer of a selectable marker to the cells. The cells are then placed under selection pressure (e.g., antibiotic resistance) so as to facilitate the isolation of those cells that have taken up, and are expressing, the transferred gene. Those cells are then delivered to a patient. In a specific embodiment, prior to the in vivo administration of the resulting recombinant cell, the nucleic acid is introduced into a cell by any method known within the art including, e.g., transfection, electroporation, microinjection, infection with a viral or bacteriophage vector containing the nucleic acid sequences of interest, cell fusion, chromosome-mediated gene transfer, microcell-mediated gene transfer, spheroplast fusion, and similar methodologies that ensure that the necessary developmental and physiological functions of the recipient cells are not disrupted by the transfer. See e.g., Loeffler and Behr, 1993. *Meth Enzymol* 217: 599-618. The chosen technique should provide for the stable transfer of the nucleic acid to the cell, such that the nucleic acid is expressible by the cell. Preferably, the transferred nucleic acid is heritable and expressible by the cell progeny.

In preferred embodiments of the present invention, the resulting recombinant cells may be delivered to a patient by various methods known within the art including, e.g., injection of epithelial cells (e.g., subcutaneously), application of recombinant skin cells as a skin graft onto the patient, and intravenous injection of recombinant blood cells (e.g., hematopoietic stem or progenitor cells). The total amount of cells that are envisioned for use depend upon the desired effect, patient state, and the like, and may be determined by one skilled within the art.

Cells into which a nucleic acid can be introduced for purposes of gene therapy encompass any desired, available cell type, and may be xenogeneic, heterogeneic, syngeneic, or autogeneic. Cell types include, but are not limited to, differentiated cells such as epithelial cells, endothelial cells, keratinocytes, fibroblasts, muscle cells, hepatocytes and blood cells, or various stem or progenitor cells, in particular embryonic heart muscle cells, liver stem cells (International Patent Publication WO 94/08598), neural stem cells (Stemple and Anderson, 1992, *Cell* 71: 973-985), hematopoietic stem or progenitor cells, e.g., as obtained from bone marrow, umbilical cord blood, peripheral blood, fetal liver, and the like. In a preferred embodiment, the cells utilized for gene therapy are autologous to the patient.

SPECIFIC EXAMPLES

Example 1

Identification of SH3 Binding Peptides

After determining that the intermediate kinase MKK7 in the JNK signaling pathway binds to the highly conserved SH3 domains of the IB1 and IB2 proteins, it was reasoned an efficient way to block the JNK signaling pathway would be to prevent the binding of the MKK7 kinase to both IB1 and IB2. Amino acid sequences important for efficient interaction with the SH3 domains of IB1 and IB2 were identified by biopanning a phage display library against GST-SH3$_{IB1/2}$ fusion proteins. The identified amino acid sequences are shown in FIG. 1. Sequence comparison between the sequences obtained during the biopanning experiment defined two conservative binding motifs SXSVGX (SEQ ID NO. 5) and PPSPRP (SEQ ID NO: 6) (FIG. 1). The latter sequence fits the PXXP SH3 binding consensus (SEQ ID NO: 35). Sequence comparison between the sequences from the biopanning experiment also revealed a consensus αSH3 sequence SVSVGMPPSPRP (SEQ ID NO: 1) and a generic αSH3 sequence SX(S/P)V(G/L)XPPSPRP (SEQ ID NO: 2). As used herein, X may be any amino acid. The single residue represented by (S/P) may be either Ser or Pro in the generic sequence. The single residue represented by (G/L) may be either Gly or Leu in the generic sequence.

Example 2

Preparation of SH3 Binding Fusion Proteins

SH3 binding fusion proteins were synthesized by covalently linking the C-terminal end of the αSH3 peptide to a N-terminal 9 amino acid long carrier peptide derived from the HIV-TAT$_{49-57}$ (Vives et al., *J. Biol. Chem.* 272: 16010 (1997)). These preparations were designated TAT (SEQ ID NO: 36) and TAT-αSH3 (SEQ ID NO: 3), respectively. All retro-inverso TAT-fusion peptides were also synthesized and were designated RV-TAT (SEQ ID NO: 38) and RV-TAT-αSH3 (SEQ ID NO: 20), respectively. All D and L peptides were produced by classical F-mock synthesis and further analyzed by Mass Spectrometry. They were finally purified by HPLC.

Generic peptides showing the conserved amino acid residues are given in Table 1. An "X" indicates any amino acid. The number of Xs in a given peptide is not limited to the one depicted, and may vary. See above for a more detailed description of the generic sequences.

Example 3

Inhibition of MKK7 Binding to IB1 and IB2 by αSH3 Peptide

Effects of the αSH3 peptide on JNK biological activities were then studied. Pull-down experiments were used to show that the –αSH3 peptide efficiently blocks the binding of MKK7 to both IB1 and IB2 (FIG. 2). In the pull-down experiments, the SH3 domains of IB1 and IB2 were subcloned using PCR into the pGEX-4T1 vector in frame with the GST (Pharmacia). The recombinant proteins were produced in *E. coli*. Purification was performed in native conditions using a glutathione-agarose column (Pharmacia). $^{35}$S-labelled MKK7 was then used in classical pull-down experiments.

Example 4

Inhibition of IL-1β-Induced Pancreatic β-Cell Death by the TAT-αSH3 Peptide

Figure 3:
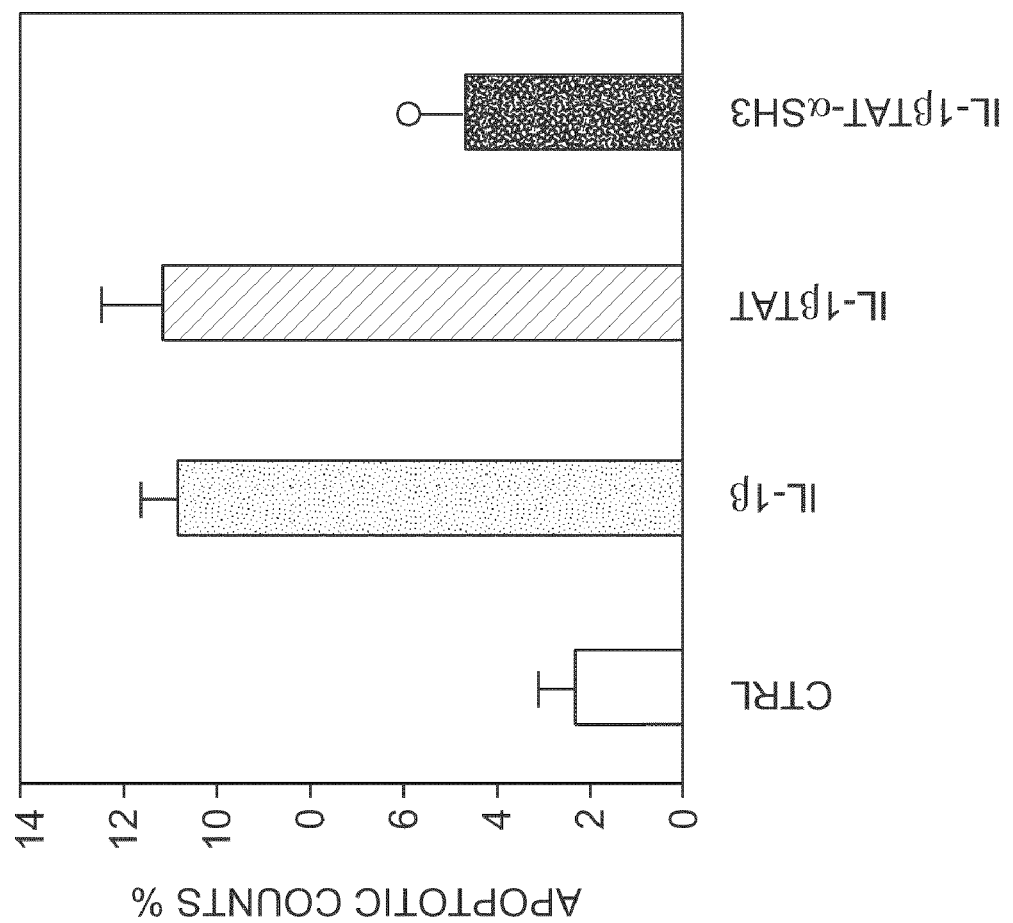
FIG. 3 is a histogram depicting inhibition of IL-1β-induced death in insulin-secreting pancreatic β-cells by the TAT-αSH3 peptide.

The effect of the TAT-αSH3 peptide construct on pancreatic β-cell apoptosis induced by IL-1β was evaluated. Pancreatic βTC-3 cells were incubated with IL-1β (10 ng/mL) for 48 hours in presence or absence of the TAT-αSH3 peptide (FIG. 3). Apoptotic counts were performed following Hoechst/PI staining, as described below. It was determined that the TAT-αSH3 peptide protects insulin-secreting cells against IL-1β-induced death.

The insulin-secreting cell lines INS-1 (Asfari et al., 1992) and βTC-3 (Efrat et al., 1988) were cultured in RPMI 1640 medium supplemented with 10% Fetal Calf Serum, 100 µg/ml Streptomycin, 100 units/ml Penicillin, 1 mM Na-pyruvate, 2 mM Glutamine and 10 mM β-mercaptoethanol. TAT, TAT-IB1 and TAT-IB2 peptides were added at a concentration of 1 μM each 30 minutes prior to the addition of IL-1β (10 ng/ml), TNF-α (10 ng/ml) or IFN-γ (100 units/ml). Apoptotic cells were counted 48 hours after the addition of the cytokines under a fluorescence microscope (Axiovert 25, Zeiss) by use of Propidium Iodide and Hoechst 33342 staining (see below). Transfection of cells was done with "lipofectamin" (Promega).

The following procedure was used to ensure an accurate measure of apoptotic β-cells. Pancreatic β-cells in cultures were prepared exactly as described in details by Hoorens et al in order to minimize pancreatic β-cells necrosis (Hoorens et al., 1996). Optical microscopy was used following staining of the cells with Hoechst 33342 (HO 342) and propidium iodide (PI) using conditions optimized for β-cells as previously described (Ammendrup et al., 2000; Hoorens et al., 1996). Using this combination of staining, viable or necrotic cells had intact nuclei with, respectively blue (HO 342) or yellow (HO 342 plus PI) fluorescence. Apoptic cells had fragmented nuclei with either a blue (HO 342) or yellow (HO 342 plus PI) fluorescence depending on the stage in the process. For the optical microscopic assays, a minimum of 1000 cells were counted for each condition. Percentages of living, necrotic and apoptotic cells were then expressed.

Example 5

Inhibition of Apoptosis in Neurons by the TAT-αSH3 Peptide

Figure 4A:
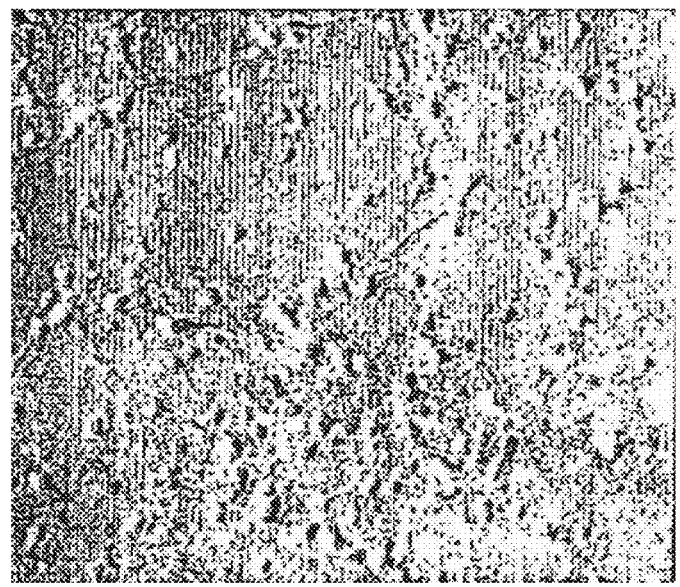
FIGS. 4A-4F are illustrations demonstrating the effects of JNK1$_{(1\ \mu M)}$ and TAT-αSH3$_{(1\ \mu M)}$ peptide on developing rat cortical neurons, as evidenced by the appearance of residual necrotic bodies (indicated as arrows). Panels B and C show the toxicity of JNK1$_{(1\ \mu M)}$ on developing rat cortical neurons, as compared to control developing rat cortical neuron shown in Panel A. Panel D shows control developing rat cortical neurons. Panels E and F show that the TAT-αSH3$_{(1\ \mu M)}$ peptide is not toxic to developing rat cortical neurons, as compared to control developing rat cortical neurons shown in Panel D.
Figure 4B:
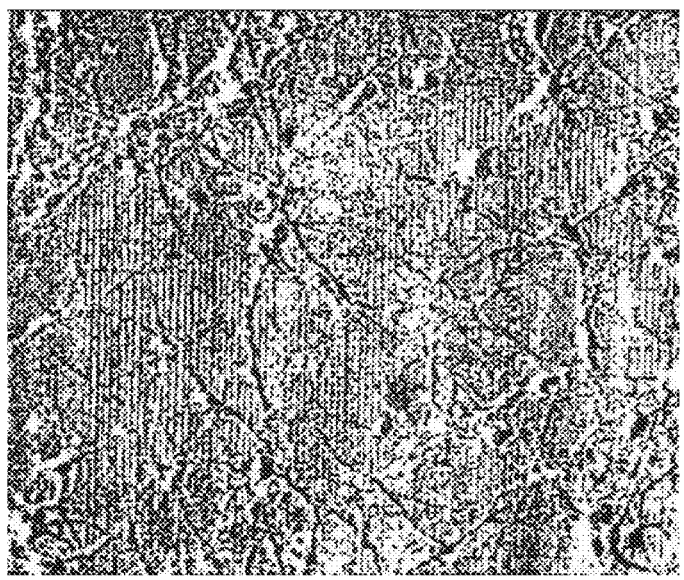
Figure 4C:
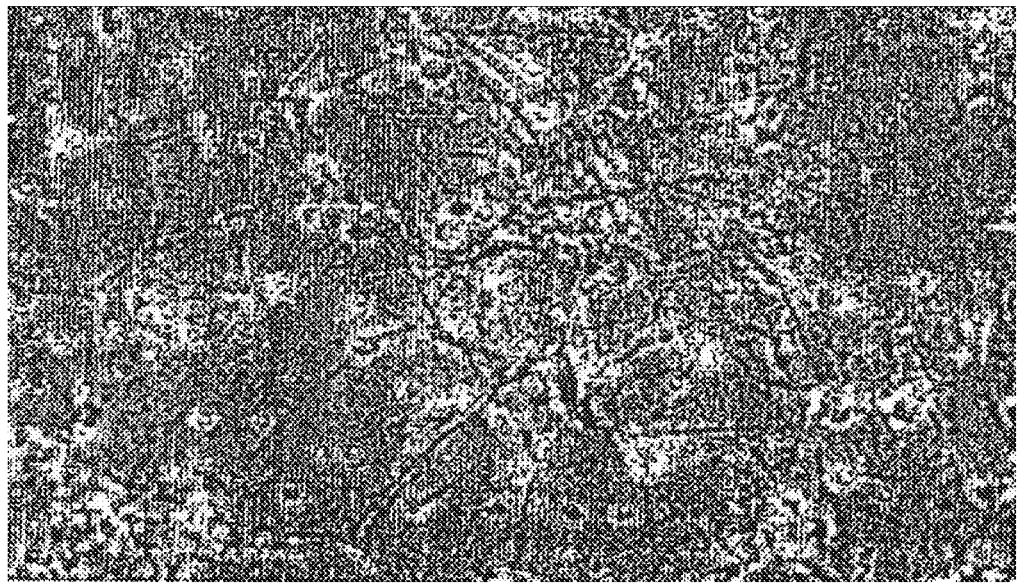
Figure 4D:
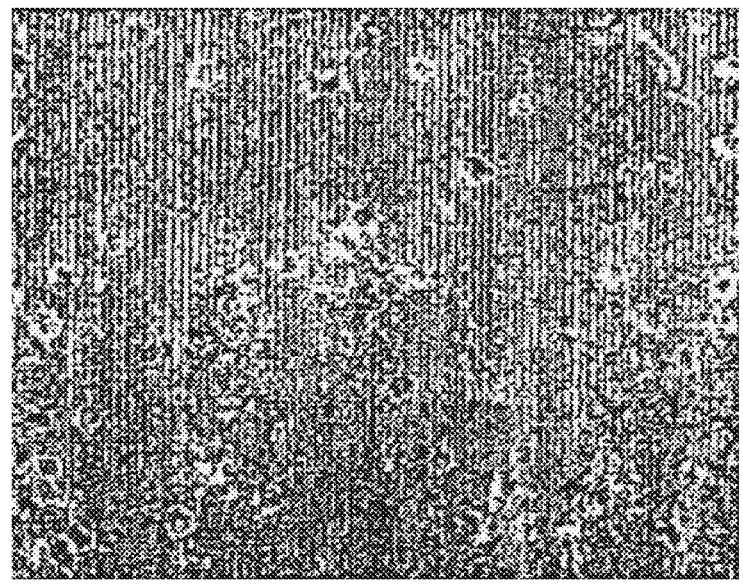
Figure 4E:
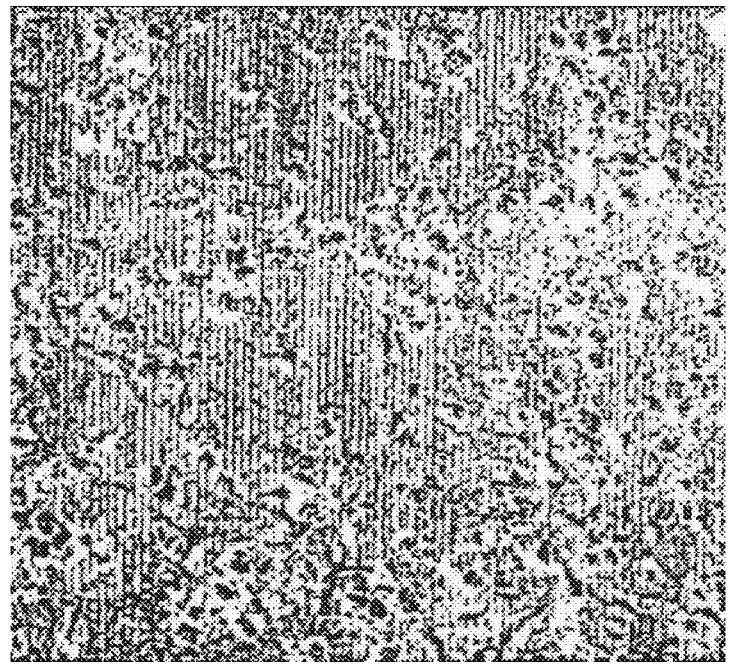
Figure 4F:
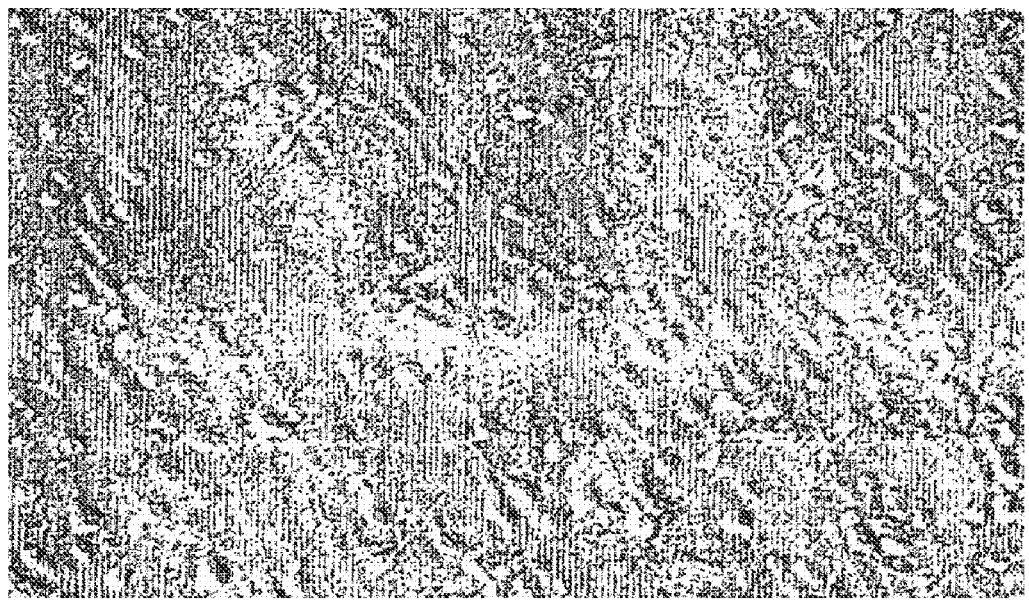

Developing rat cortical neurons were incubated with either $JNKI_{(1\,\mu M)}$ (FIG. 4A-4C) or TAT-αSH3$_{(1\,\mu M)}$ (FIGS. 4D-4F). When compared with control developing rat cortical neurons (FIG. 4A), JNKI was found to be toxic on the developing neurons, as evidenced by the appearance of residual necrotic bodies (indicated by arrows) (FIG. 4B-4C). The neurons incubated in the presence of TAT-αSH3$_{(1\,\mu M)}$ lacked residual necrotic bodies (FIG. 4E-4F), when compared to control developing rat cortical neurons (FIG. 4C).

It was also found that the TAT-αSH3 peptide (FIG. 4E) reproducibly increased the number of developing neurons obtained over controls (FIG. 4D).

Example 6

Inhibition of NMDA-Induced Apoptosis in Neurons by the TAT-αSH3 Peptide

Figure 5A:
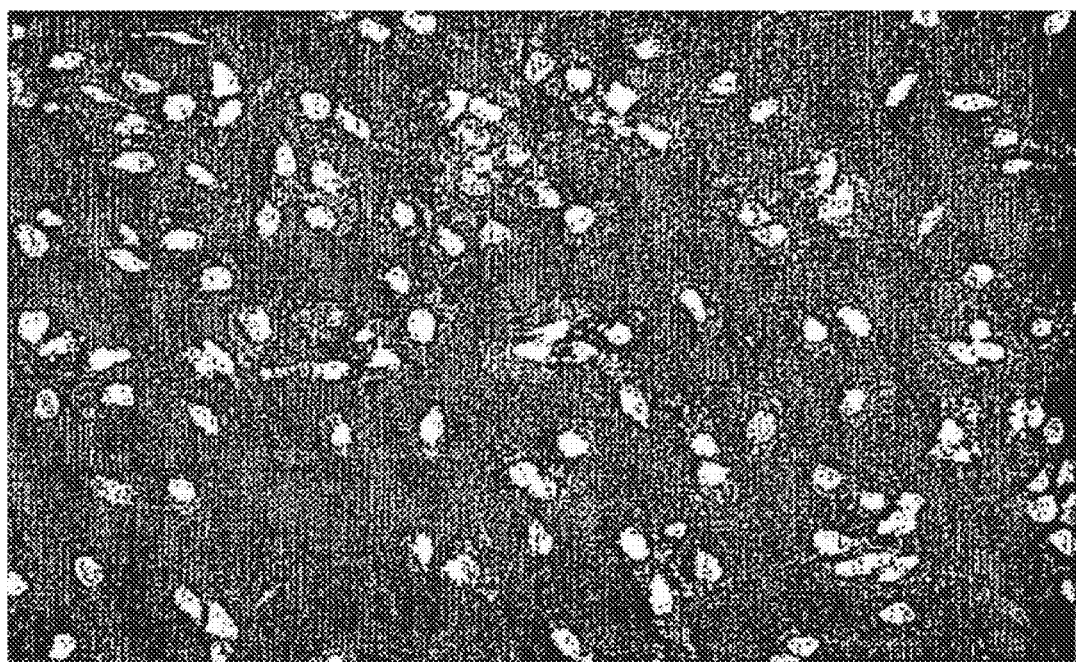
FIG. 5A is an illustration demonstrating the inhibition of NMDA-induced death by the TAT-αSH3$_{(1\ \mu M)}$ peptide in neurons stained with Hoechst/PI.
Figure 5B:
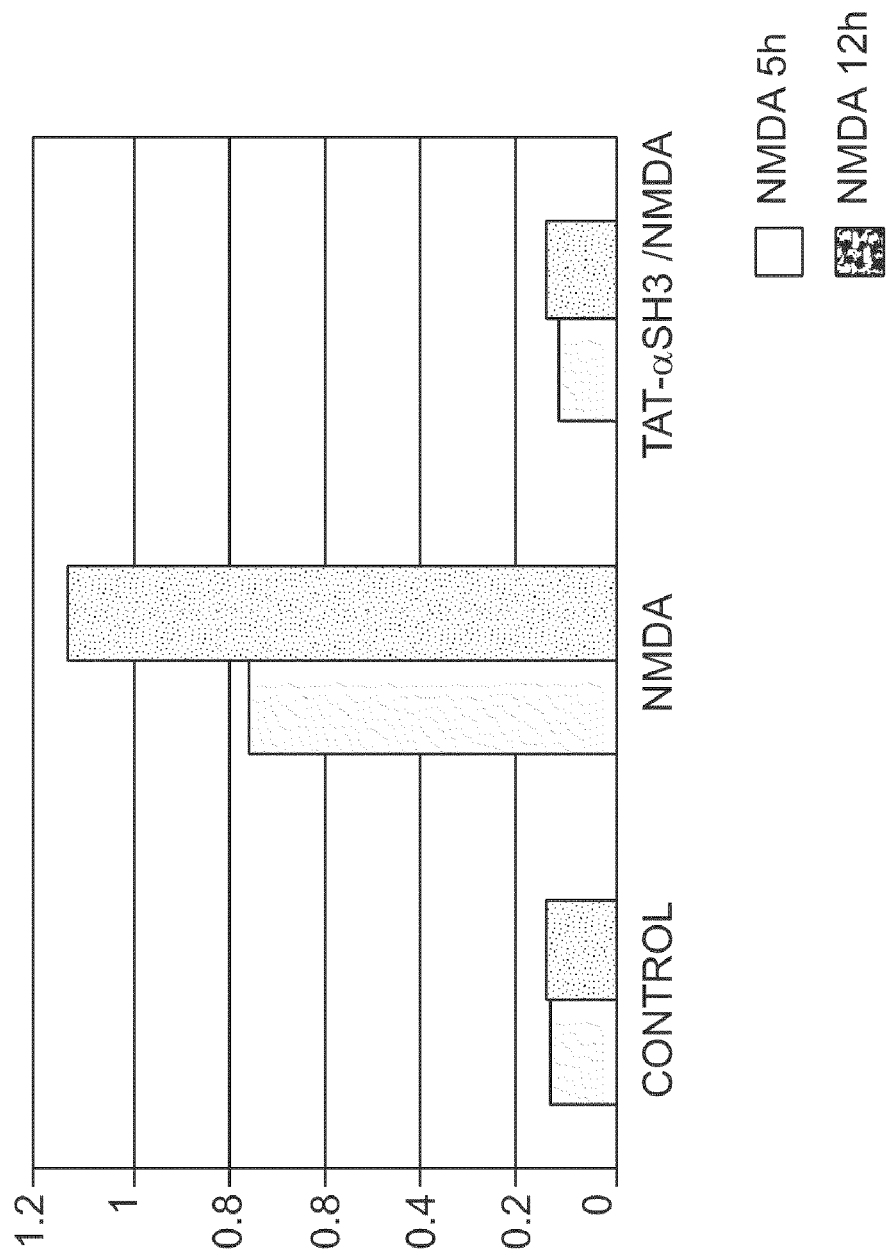
FIG. 5B is a histogram demonstrating the inhibition of NMDA-induced death by the TAT-αSH3$_{(1\ \mu M)}$ peptide in neurons stained with lactate dehydrogenase (LDH).

Rat cortical neurons in culture were incubated with N-methyl-D-aspartate (NMDA), either with or without the TAT-αSH3$_{(1\,\mu M)}$ peptide. The cells were then stained with either Hoechst/PI (FIG. 5A), or with lactate dehydrogenase (LDH). The level of LDH released in the medium was measured to quantify cell death (FIG. 5B). It was found that the TAT-αSH3 peptide completely protected neurons against NMDA-induced death.

Example 7

In Vitro Solid Phase JNK Assays

βTC-3 and other insulin-secreting cells will be activated by cytokine treatment before being used for cell extract preparation and processed as described (Bonny et al., 2000). Briefly, cellular extracts will be prepared by scraping control and activated cells in lysis buffer (20 mM Tris-acetate, 1 mM EGTA, 1% Triton X-100, 10 mM p-nitrophenyl-phosphate (pNPP), 5 mM sodium pyrophosphate, 10 mM β-glycerophosphate, 1 mM dithiothreitol). Debris will be removed by centrifugation for 5' at 15'000 rpm in an SS-34 rotor (Beckman). 100 μg extracts will be incubated for 1 hour at 4° C. with 1 μg GST-Jun (amino acids 1-89) or other GST-fusion proteins and 10 μl of gluthathione-agarose beads (Sigma). Following 4 washes with the scraping buffer, the beads will be resuspended in the same buffer supplemented with 10 mM $MgCL_2$ and 5 μCiγ$^{33}$P-ATP and incubated for 30 minutes at 30° C. Reaction products will then be separated by SDS-PAGE on a denaturing 12% polyacrylamide gel. The gels will be dried and subsequently exposed to X-Ray films (Kodak).

Recombinant JNKs will be produced in a reticulocyte transcription/translation system (Promega). The relevant domains of bcl-2, bcl-$x_L$, p53, c-myc, PPARγ, tau and IRS-1 will be subcloned using PCR into the pGEX-4T1 vector in frame with the GST (Pharmacia). The recombinant proteins will be produced in *E. coli* and purified in native conditions using a glutathione-agarose column (Pharmacia). Kinase assays will be performed by mixing the recombinant JNKs and GST-substrates as described in details (Bonny et al., 2001).

Example 8

Synthesis of an All-D-Retro-Inverso Peptides

Peptides of the invention may be all-D amino acid peptides synthesized in reverse to prevent natural proteolysis (i.e., all-D-retro-inverso peptides). An all-D retro-inverso peptide of the invention would provide a peptide with functional properties similar to the native peptide, wherein the side groups of the component amino acids would correspond to the native peptide alignment, but would retain a protease resistant backbone.

Retro-inverso peptides of the invention are analogs synthesized using D-amino acids by attaching the amino acids in a peptide chain such that the sequence of amino acids in the retro-inverso peptide analog is exactly opposite of that in the selected peptide which serves as the model. To illustrate, if the naturally occurring TAT protein (formed of L-amino acids) has the sequence RKKRRQRRR (SEQ ID NO: 36), the retro-inverso peptide analog of this peptide (formed of D-amino acids) would have the sequence RRRQRRKKR (SEQ ID NO: 38). The procedures for synthesizing a chain of D-amino acids to form the retro-inverso peptides are known in the art. See, e.g., Jameson et al., Nature, 368, 744-746 (1994); Brady et al, *Nature*, 368, 692-693 (1994)); Guichard et al., J. Med. Chem. 39, 2030-2039 (1996). Specifically, the retro-peptides are produced by classical F-mock synthesis and further analyzed by Mass Spectrometry. They are finally purified by HPLC.

Since an inherent problem with native peptides is degradation by natural proteases and inherent immunogenicity, the heterobivalent or heteromultivalent compounds of this invention will be prepared to include the "retro-inverso isomer" of the desired peptide. Protecting the peptide from natural proteolysis should therefore increase the effectiveness of the specific heterobivalent or heteromultivalent compound, both by prolonging half-life and decreasing the extent of the immune response aimed at actively destroying the peptides.

Other Embodiments

While the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method of inhibiting apoptosis in a neuronal cell or a pancreatic cell, comprising contacting said cell with a chimeric peptide less than 50 amino acids in length, wherein the peptide comprises a first domain and a second domain linked by a covalent bond, wherein said first domain comprises the amino acid sequence of SEQ ID NO:38 and the second domain comprises the amino acid sequence of SEQ ID NO:2, wherein Xaa at the amino acid residue positions 2 and 6 can be any single amino acid, Xaa at the amino acid residue 3 position can be either serine or proline, Xaa at the amino acid residue 5 position can be either glycine or leucine, and wherein said chimeric peptide inhibits the binding of mitogen-activated protein kinase-7 (MKK7) to insulin binding protein 1 (IB1) or insulin binding protein 2 (IB2).

2. The method of claim 1, wherein said cell is provided in vitro, in vivo or ex vivo.

3. A method of promoting neuronal cell growth, comprising contacting said cell with a chimeric peptide less than 50 amino acids in length, wherein the peptide comprises a first domain and a second domain linked by a covalent bond, wherein said first domain comprises the amino acid sequence of SEQ ID NO:38 and the second domain comprises the amino acid sequence of SEQ ID NO:2, wherein Xaa at the amino acid residue positions 2 and 6 can be any single amino acid, Xaa at the amino acid residue 3 position can be either serine or proline, Xaa at the amino acid residue 5 position can be either glycine or leucine, and wherein said chimeric peptide inhibits the binding of mitogen-activated protein kinase-7 (MKK7) to insulin binding protein 1 (IB1) or insulin binding protein 2 (IB2).

4. The method of claim 3, wherein said cell is provided in vitro, in vivo or ex vivo.

* * * * *

SEQUENCE LISTING

<160> NUMBER OF SEQ ID NOS: 40

<210> SEQ ID NO 1
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Ser Val Ser Val Gly Met Pro Pro Ser Pro Arg Pro
1               5                   10

<210> SEQ ID NO 2
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Variable amino acid
<220> FEATURE:
<221> NAME/KEY: MOD_RES
<222> LOCATION: (3)..(3)
<223> OTHER INFORMATION: Ser or Pro
<220> FEATURE:
<221> NAME/KEY: MOD_RES
<222> LOCATION: (5)..(5)
<223> OTHER INFORMATION: Gly or Leu
<220> FEATURE:
<221> NAME/KEY: MOD_RES
<222> LOCATION: (6)..(6)
<223> OTHER INFORMATION: Variable amino acid

<400> SEQUENCE: 2

Ser Xaa Xaa Val Xaa Xaa Pro Pro Ser Pro Arg Pro
1               5                   10

<210> SEQ ID NO 3
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Arg Lys Lys Arg Arg Gln Arg Arg Arg Ser Val Ser Val Gly Met Pro
1               5                   10                  15

Pro Ser Pro Arg Pro
            20

<210> SEQ ID NO 4
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(4)
<223> OTHER INFORMATION: Variable amino acid
<220> FEATURE:
<221> NAME/KEY: MOD_RES
<222> LOCATION: (14)..(17)

```
<223> OTHER INFORMATION: Variable amino acid
<220> FEATURE:
<221> NAME/KEY: MOD_RES
<222> LOCATION: (19)..(19)
<223> OTHER INFORMATION: Variable amino acid
<220> FEATURE:
<221> NAME/KEY: MOD_RES
<222> LOCATION: (20)..(20)
<223> OTHER INFORMATION: Ser or Pro
<220> FEATURE:
<221> NAME/KEY: MOD_RES
<222> LOCATION: (22)..(22)
<223> OTHER INFORMATION: Gly or Leu
<220> FEATURE:
<221> NAME/KEY: MOD_RES
<222> LOCATION: (23)..(23)
<223> OTHER INFORMATION: Variable amino acid

<400> SEQUENCE: 4

Xaa Xaa Xaa Xaa Arg Lys Lys Arg Arg Gln Arg Arg Xaa Xaa Xaa
1               5                   10                  15

Xaa Ser Xaa Xaa Val Xaa Xaa Pro Pro Ser Pro Arg Pro
            20                  25

<210> SEQ ID NO 5
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Variable amino acid
<220> FEATURE:
<221> NAME/KEY: MOD_RES
<222> LOCATION: (6)..(6)
<223> OTHER INFORMATION: Variable amino acid

<400> SEQUENCE: 5

Ser Xaa Ser Val Gly Xaa
1               5

<210> SEQ ID NO 6
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Pro Pro Ser Pro Arg Pro
1               5

<210> SEQ ID NO 7
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Ser Val Ser Val Gly Met Lys Pro Ser Pro Arg Pro
1               5                   10

<210> SEQ ID NO 8
<211> LENGTH: 12
<212> TYPE: PRT
```

```
<213> ORGANISM: Artificial Sequence
<220> FEATURE:
<223> OTHER INFORMATION: Description of Artificial Sequence: Synthetic
      peptide

<400> SEQUENCE: 8

Ser Val Ser Val Gly Lys Asn Pro Ser Pro Arg His
1               5                   10

<210> SEQ ID NO 9
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Thr Gln Pro Met Met Ala Pro Pro Ser Pro Arg Gln
1               5                   10

<210> SEQ ID NO 10
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Leu Asp Ser Leu Cys His Pro Gln Ser Pro Arg Pro
1               5                   10

<210> SEQ ID NO 11
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

His Pro Phe Leu Val Ser Ser Ser Pro Arg Pro
1               5                   10

<210> SEQ ID NO 12
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Gly Gln Pro Phe Phe Ser Pro Phe Ser
1               5

<210> SEQ ID NO 13
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

Pro Pro Ser Asn Leu Ile Pro Pro Thr Leu Arg
1               5                   10
```

<210> SEQ ID NO 14
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

Ser Pro Pro Ser Asn Leu
1               5

<210> SEQ ID NO 15
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

Phe Asn Pro Trp Ser Ser Lys Pro Ser Leu Leu
1               5                   10

<210> SEQ ID NO 16
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

Asn Ala Ser Val Gly Asn Asp His Ser His Ser His
1               5                   10

<210> SEQ ID NO 17
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17

Glu His Met Ala Leu Thr Tyr Pro Phe Arg Pro
1               5                   10

<210> SEQ ID NO 18
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18

Pro Arg Pro Ser Pro Pro Met Gly Val Ser Val Ser
1               5                   10

<210> SEQ ID NO 19
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES -continued

```
<222> LOCATION: (7)..(7)
<223> OTHER INFORMATION: Variable amino acid
<220> FEATURE:
<221> NAME/KEY: MOD_RES
<222> LOCATION: (8)..(8)
<223> OTHER INFORMATION: Gly or Leu
<220> FEATURE:
<221> NAME/KEY: MOD_RES
<222> LOCATION: (10)..(10)
<223> OTHER INFORMATION: Ser or Pro
<220> FEATURE:
<221> NAME/KEY: MOD_RES
<222> LOCATION: (11)..(11)
<223> OTHER INFORMATION: Variable amino acid

<400> SEQUENCE: 19

Pro Arg Pro Ser Pro Pro Xaa Xaa Val Xaa Xaa Ser
1               5                   10

<210> SEQ ID NO 20
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 20

Pro Arg Pro Ser Pro Pro Met Gly Val Ser Val Ser Arg Arg Gln
1               5                   10                  15

Arg Arg Lys Lys Arg
            20

<210> SEQ ID NO 21
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (7)..(7)
<223> OTHER INFORMATION: Variable amino acid
<220> FEATURE:
<221> NAME/KEY: MOD_RES
<222> LOCATION: (8)..(8)
<223> OTHER INFORMATION: Gly or Leu
<220> FEATURE:
<221> NAME/KEY: MOD_RES
<222> LOCATION: (10)..(10)
<223> OTHER INFORMATION: Ser or Pro
<220> FEATURE:
<221> NAME/KEY: MOD_RES
<222> LOCATION: (11)..(11)
<223> OTHER INFORMATION: Variable amino acid
<220> FEATURE:
<221> NAME/KEY: MOD_RES
<222> LOCATION: (13)..(16)
<223> OTHER INFORMATION: Variable amino acid
<220> FEATURE:
<221> NAME/KEY: MOD_RES
<222> LOCATION: (26)..(29)
<223> OTHER INFORMATION: Variable amino acid

<400> SEQUENCE: 21

Pro Arg Pro Ser Pro Pro Xaa Xaa Val Xaa Xaa Ser Xaa Xaa Xaa Xaa
1               5                   10                  15

Arg Arg Arg Gln Arg Arg Lys Lys Arg Xaa Xaa Xaa Xaa
            20                  25

<210> SEQ ID NO 22
```

```
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Variable amino acid
<220> FEATURE:
<221> NAME/KEY: MOD_RES
<222> LOCATION: (5)..(5)
<223> OTHER INFORMATION: Variable amino acid

<400> SEQUENCE: 22

Xaa Gly Val Ser Xaa Ser
1               5

<210> SEQ ID NO 23
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 23

Pro Arg Pro Ser Pro Pro
1               5

<210> SEQ ID NO 24
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 24

Pro Arg Pro Ser Pro Lys Met Gly Val Ser Val Ser
1               5                   10

<210> SEQ ID NO 25
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 25

His Arg Pro Ser Pro Asn Lys Gly Val Ser Val Ser
1               5                   10

<210> SEQ ID NO 26
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 26

Gln Arg Pro Ser Pro Pro Ala Met Met Pro Gln Thr
1               5                   10

<210> SEQ ID NO 27
<211> LENGTH: 12
<212> TYPE: PRT
```

```
<213> ORGANISM: Artificial Sequence
<220> FEATURE:
<223> OTHER INFORMATION: Description of Artificial Sequence: Synthetic
      peptide

<400> SEQUENCE: 27

Pro Arg Pro Ser Gln Pro His Cys Leu Ser Asp Leu
1               5                   10

<210> SEQ ID NO 28
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 28

Pro Arg Pro Ser Ser Ser Val Leu Phe Pro His
1               5                   10

<210> SEQ ID NO 29
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 29

Ser Phe Pro Ser Phe Phe Pro Gln Gly
1               5

<210> SEQ ID NO 30
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 30

Arg Leu Thr Pro Pro Ile Leu Asn Ser Pro Pro
1               5                   10

<210> SEQ ID NO 31
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 31

Leu Asn Ser Pro Pro Ser
1               5

<210> SEQ ID NO 32
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 32

Leu Leu Ser Pro Lys Ser Ser Trp Pro Asn Phe
1               5                   10
```

```
<210> SEQ ID NO 33
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 33

His Ser His Ser His Asp Asn Gly Val Ser Ala Asn
1               5                   10

<210> SEQ ID NO 34
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 34

Pro Arg Phe Pro Tyr Thr Leu Ala Met His Glu
1               5                   10

<210> SEQ ID NO 35
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(3)
<223> OTHER INFORMATION: Variable amino acid

<400> SEQUENCE: 35

Pro Xaa Xaa Pro
1

<210> SEQ ID NO 36
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 36

Arg Lys Lys Arg Arg Gln Arg Arg Arg
1               5

<210> SEQ ID NO 37
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Variable amino acid and can represent any
      number of amino acid residues, including zero
<220> FEATURE:
<221> NAME/KEY: MOD_RES
<222> LOCATION: (11)..(11)
<223> OTHER INFORMATION: Variable amino acid and can represent any
      number of amino acid residues, including zero

<400> SEQUENCE: 37
```

```
Xaa Arg Lys Lys Arg Arg Gln Arg Arg Xaa
1               5                   10

<210> SEQ ID NO 38
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 38

Arg Arg Arg Gln Arg Arg Lys Lys Arg
1               5

<210> SEQ ID NO 39
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Variable amino acid and can represent any
      number of amino acid residues, including zero
<220> FEATURE:
<221> NAME/KEY: MOD_RES
<222> LOCATION: (11)..(11)
<223> OTHER INFORMATION: Variable amino acid and can represent any
      number of amino acid residues, including zero

<400> SEQUENCE: 39

Xaa Arg Arg Arg Gln Arg Arg Lys Lys Arg Xaa
1               5                   10

<210> SEQ ID NO 40
<211> LENGTH: 56
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 40

Pro Lys Val Val Ala Leu Tyr Asp Tyr Gln Ala Arg Glu Ser Asp Glu
1               5                   10                  15

Leu Ser Phe Lys Lys Gly Asp Ile Ile Ile Val Leu Glu Lys Ser Asp
            20                  25                  30

Asp Gly Trp Trp Lys Gly Arg Leu Lys Gly Thr Lys Glu Gly Leu Ile
        35                  40                  45

Pro Ser Asn Tyr Val Glu Pro Val
    50                  55
```